(12) United States Patent
Kon et al.

(10) Patent No.: US 8,901,280 B2
(45) Date of Patent: *Dec. 2, 2014

(54) ANTIBODY AGAINST RGD IN AMINO ACID SEQUENCE OF EXTRACELLULAR MATRIX PROTEIN AND PRODUCTION METHOD AND USE OF THE SAME

(75) Inventors: Shigeyuki Kon, Hokkaido (JP); Chiemi Kimura, Hokkaido (JP); Toshimitsu Uede, Hokkaido (JP)

(73) Assignee: Gene Techno Science Co., Ltd., Hokkaido (JP)

(*) Notice: Subject to any disclaimer, the term of this patent is extended or adjusted under 35 U.S.C. 154(b) by 703 days.

This patent is subject to a terminal disclaimer.

(21) Appl. No.: 12/312,022

(22) PCT Filed: Oct. 25, 2007

(86) PCT No.: PCT/JP2007/071279
§ 371 (c)(1),
(2), (4) Date: Feb. 2, 2010

(87) PCT Pub. No.: WO2008/050907
PCT Pub. Date: May 2, 2008

(65) Prior Publication Data
US 2011/0065899 A1 Mar. 17, 2011

(30) Foreign Application Priority Data
Oct. 26, 2006 (JP) ................................. 2006-290737

(51) Int. Cl.
| | | |
|---|---|---|
| *C07K 16/18* | (2006.01) | |
| *A61K 39/395* | (2006.01) | |
| *C12N 5/12* | (2006.01) | |
| *C12N 15/13* | (2006.01) | |
| *A61P 35/00* | (2006.01) | |
| *A61P 29/00* | (2006.01) | |
| *A61P 19/10* | (2006.01) | |
| *A61P 31/12* | (2006.01) | |
| *C07K 16/44* | (2006.01) | |
| *G01N 33/68* | (2006.01) | |
| *G01N 33/574* | (2006.01) | |
| *A61K 39/00* | (2006.01) | |

(52) U.S. Cl.
CPC .......... *C07K 16/18* (2013.01); *C07K 2317/565* (2013.01); *C07K 2316/96* (2013.01); *G01N 2800/108* (2013.01); *G01N 2800/102* (2013.01); *C07K 16/44* (2013.01); *G01N 2800/26* (2013.01); *G01N 33/6893* (2013.01); *G01N 2800/24* (2013.01); *G01N 2800/105* (2013.01); *G01N 33/574* (2013.01); *A61K 2039/505* (2013.01); *C07K 2317/34* (2013.01)
USPC ............... 530/388.2; 530/387.3; 530/387.9; 424/133.1; 424/152.1; 435/332; 435/69.6; 514/16.9; 514/19.3; 514/4.3

(58) Field of Classification Search
None
See application file for complete search history.

(56) References Cited

U.S. PATENT DOCUMENTS

| | | | |
|---|---|---|---|
| 5,530,101 | A | 6/1996 | Queen et al. |
| 5,859,205 | A | 1/1999 | Adair et al. |
| 7,241,873 | B2 | 7/2007 | Uede et al. |
| 2004/0234524 | A1 | 11/2004 | Uede et al. |
| 2004/0234525 | A1 | 11/2004 | Uede et al. |
| 2006/0002923 | A1 | 1/2006 | Uede et al. |

FOREIGN PATENT DOCUMENTS

| | | |
|---|---|---|
| EP | 1 375 518 A1 | 1/2004 |
| EP | 1 637 159 A1 | 3/2006 |
| WO | WO 97/11718 A1 | 4/1997 |
| WO | WO 00/63241 A2 | 10/2000 |
| WO | WO 01/71358 A1 | 9/2001 |
| WO | WO 02/081522 A1 | 10/2002 |
| WO | WO 03/027151 A1 | 4/2003 |
| WO | WO 2008/050907 A1 | 5/2008 |

OTHER PUBLICATIONS

Rudikoff, Giusti, Cook, and Scharff. Single amino acid substitution altering antigen binding specificity. Proceedings of the National Academy of Sciences, 1982. vol. 79, pp. 1979-1983.*

Mac Callum, Martin, and Thornton. Antibody antigen interactions: contact analysis and binding site topography. Journal of Molecular Biology, 1996. vol. 262, pp. 732-745.*

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Vajdos, Adams, Breece, Presta, De Vos, and Sidhu. Comprehensive functional maps of the antigen binding site of an anti-ErbB2 antibody obtained with shotgun scanning mutagenesis. Journal of Molecular Biology, 2002. vol. 320, pp. 415-428.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

(Continued)

*Primary Examiner* — Misook Yu
*Assistant Examiner* — Michael D Allen
(74) *Attorney, Agent, or Firm* — Foley & Lardner LLP

(57) ABSTRACT

The present invention provides a monoclonal antibody which specifically recognizes RGD in the amino acid sequence of extracellular matrix proteins of a human and a mouse. By specifically inhibiting the RGD sequence-mediated adhesion, exertion of efficient effects on diseases such as inflammation, cancer, infectious disease, autoimmune diseases and osteoporosis and reduction in adverse effects can be expected at the same time. Therefore, better treatment methods can be provided to these diseases.

14 Claims, 14 Drawing Sheets

(56) References Cited

OTHER PUBLICATIONS

Wu, Nie, Huse, and Watkins. Humanization of a murine monoclonal antibody by simultaneous optimization of framework and CDR residues. Journal of Molecular Biology, 1999. vol. 294, pp. 151-162.*

Osbourn et al., 2003, Drug Discovery Today, vol. 8, No. 18, p. 845-851.*

Johnson et Al., 2004, Antibody Engineering: Methods and Protocols, p. 11-25.*

International Search Report mailed Dec. 4, 2007 in PCT/JP2007/071279, 5 pages.

Green et al., "Antibody engineering via genetic engineering of the mouse: XenoMouse strains are a vehicle for the facile generation of therapeutic human monoclonal antibodies," Journal of Immunological Methods, 1999, 231:11-23.

Supplementary European Search Report dated Jul. 7, 2010, in corresponding EP 07831013.3, 10 pages.

Kon et al., "Mapping of Functional Epitopes of Osteopontin by Monoclonal Antibodies Raised Against Defined Internal Sequences," Journal of Cellular Biochemistry, Oct. 15, 2001, 84(2):420-432.

U.S. Appl. No. 12/989,208, filed Apr. 24, 2009, Kumar et al.

Frisch et al., "Integrins and anoikis," Curr. Opin. Cell Biol., 1997, 9:701-706.

Giancotti et al., "Integrin Signaling," Science, Aug. 13, 1999, 285:1028-1032.

Gu et al., "Laminin-10/11 and Fibronectin Differentially Regulate Integrin-dependent Rho and Rac Activation via $p130^{Cas}$-CrkII-DOCK180 Pathway," J. Biol. Chem., Jul. 20, 2001, 276(29):27090-27097.

Gu et al., "Laminin-10/11 and Fibronectin Differentially Prevent Apoptosis Induced by Serum via Phosphatidylinositol 3-Kinase/Akt- and MEK1/ERK-dependent Pathways," J. Biol. Chem., May 31, 2002, 277(22):19922-19928.

Vassilev et al., "Inhibition of Cell Adhesion by Antibodies to Arg-Gly-Asp (RGD) in Normal Immunoglobulin for Therapeutic Use (Intravenous Immunoglobulin, IVIg)," Blood, Jun. 1, 1999, 93(11):3624-3631.

U.S. Appl. No. 13/497,692, filed Mar. 22, 2012, Kumar et al.

Yamamoto et al., "Successful treatment of collagen-induced arthritis in non-human primates by chimeric anti-osteopontin antibody," International Immunopharmacology, 2007, 7:1460-1470.

Beiboer et al., "Guided Selection of a Pan Carcinoma Specific Antibody Reveals Similar Binding Characteristics yet Structural Divergence Between the Original Murine Antibody and its Human Equivalent," J. Mol. Biol., 2000, 296:833-849.

Brown et al., "Tolerance to Single, but Not Multiple, Amino Acid Replacements in Antibody $V_H$CDR2," J. Immunol., 1996, 156:3285-3291.

Klimka et al., "Human anti-CD30 recombinant antibodies by guided phage antibody selection using cell panning," British Journal of Cancer, 2000, 83(2):252-260.

Padlan, Eduardo A., "Anatomy of the Antibody Molecule," Molecular Immunology, 1994, 31(3):169-217.

Paul, William E., M.D., Ed., Fundamental Immunology, Third Edition, 1993, 292-295.

Tsurushita et al., "Design of humanized antibodies: From anti-Tac to Zenapax," Methods, 2005, 36:69-83.

Almagro et al., "Humanization of antibodies," Frontiers in Bioscience, Jan. 1, 2008, 13:1619-1633.

* cited by examiner

Fig. 12
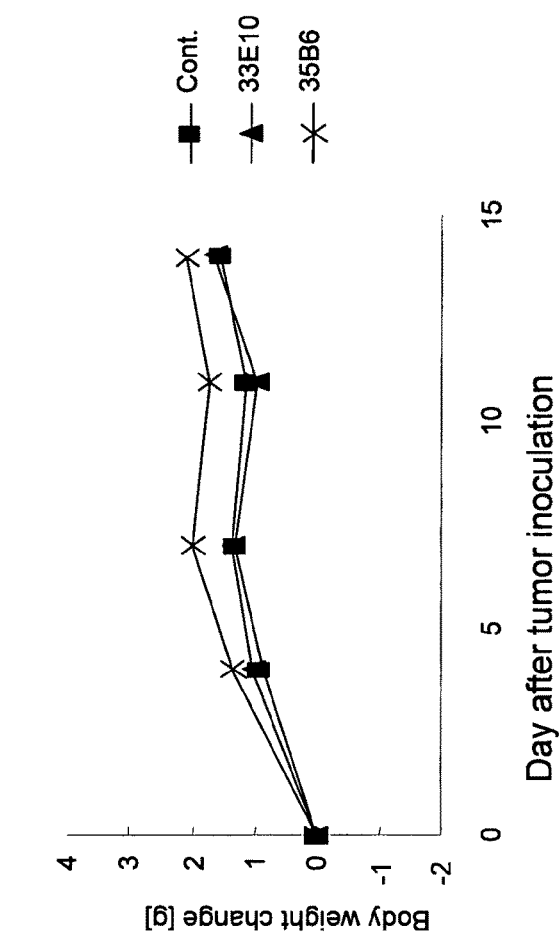
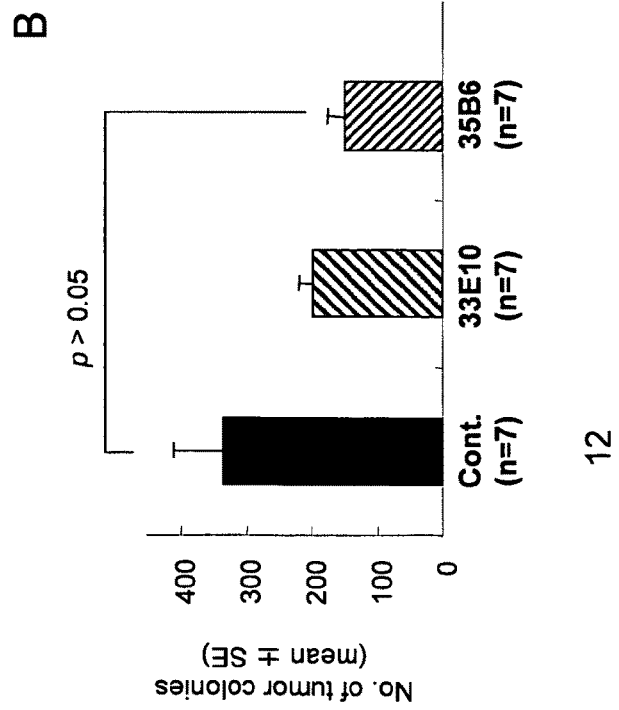

SEQUENCE LISTING

```
<160> NUMBER OF SEQ ID NOS: 38

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Thr Asp Tyr Tyr Met Ile
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Thr Phe Thr Asn Tyr Trp Met His
1               5                   10

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Leu Gly Phe Ile Arg Asn Lys Ala Asn Gly Tyr Thr Thr Glu Tyr
1               5                   10                  15

Ser Ala Ser Val Lys Gly
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 4

Trp Ile Gly Asn Ile Asn Pro Arg Asn Gly Asp Ser Asn Tyr Asn Glu
1               5                   10                  15

Lys Phe Arg Ser
            20

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ala Tyr
1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Phe Asp Val
1               5

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Ser Gln Ser Ile Val His Ser Asn Gly Asn Thr Tyr Leu Glu
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ala Ser Gln Asp Ile Asn Ser Tyr Leu Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Val Ser Asn Arg Phe Ser
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Asn Arg Leu Val Asp
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Phe Val Pro Trp
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Asp Glu Phe Pro Phe
1               5

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Val Asp Val Pro Asn Gly Arg Gly Asp Ser Leu Ala Tyr Gly Leu
1               5                   10                  15

Arg

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Leu Pro Val Lys Thr Asp Ser Gly Ser Ser Glu Glu Lys Leu Tyr
1               5                   10                  15

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 15

Cys Val Asp Val Pro Asn Gly Arg Gly Asp Ser
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Pro Asn Gly Arg Gly Asp
1               5

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Gly Arg Gly Asp Ser Leu Ala Tyr Gly Leu Arg
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Gly Asp Ser Leu Ala Tyr Gly
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Gly Asp Ser Leu Ala Tyr Gly Leu Arg
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Ser Leu Ala Tyr Gly Leu Arg
1               5

<210> SEQ ID NO 21
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Val Asp Thr Tyr Asp Gly Arg Gly Asp Ser Val Val Tyr Gly Leu
1               5                   10                  15
Arg Ser

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Ser Val Val Tyr Gly Leu Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Gly Arg Gly Asp Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Arg Gly Asp Ser
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Leu Ala Tyr Gly Leu Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

Ser Val Val Tyr Gly Leu Arg
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Asp Val Pro Asn Gly Arg Gly Asp Ser Leu Ala Tyr Gly Leu Arg
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Pro Val Lys Val Thr Asp Ser Gly Ser Ser Glu Glu Lys Leu Tyr
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Asp Thr Tyr Asp Gly Arg Gly Asp Ser Val Val Tyr Gly Leu Arg
1               5                   10                  15
Ser

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Asp Val Pro Asn Gly Arg Gly Asp Ser
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Arg Gly Asp Ser Leu Ala Tyr Gly Leu Arg
1               5                   10

<210> SEQ ID NO 32
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Asn Gly Arg Gly Asp
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Asp Ser Leu Ala Tyr Gly
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Asp Ser Leu Ala Tyr Gly Leu Arg
1               5

<210> SEQ ID NO 35
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Val Lys Leu Gln Glu Ser Gly Gly Gly Leu Val Gln Pro Gly Gly Ser
1               5                   10                  15

Leu Ser Leu Ser Cys Ala Ala Ser Gly Phe Thr Phe Thr Asp Tyr Tyr
            20                  25                  30

Met Ile Trp Val Arg Gln Pro Pro Gly Lys Ala Leu Glu Trp Leu Gly
        35                  40                  45

Phe Ile Arg Asn Lys Ala Asn Gly Tyr Thr Thr Glu Tyr Ser Ala Ser
    50                  55                  60

Val Lys Gly Arg Phe Thr Ile Ser Arg Asp Asn Ser Gln Ser Ile Leu
65                  70                  75                  80

Tyr Leu Gln Met Asn Ala Leu Arg Ala Glu Asp Ser Ala Thr Tyr Tyr
                85                  90                  95

Cys Ala Phe Gly Ala Tyr Trp Gly Gln Gly Thr Thr Val Thr Val Ser
                100                 105                 110

Ser

<210> SEQ ID NO 36
<211> LENGTH: 113
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 36

Val Lys Leu Gln Glu Ser Gly Thr Glu Leu Val Lys Pro Gly Ala Ser
1               5                   10                  15

Val Lys Leu Ser Cys Lys Ala Ser Gly Tyr Thr Phe Thr Asn Tyr Trp
            20                  25                  30

Met His Trp Val Lys Gln Arg Pro Gly Gln Gly Leu Glu Trp Ile Gly
        35                  40                  45

Asn Ile Asn Pro Arg Asn Gly Asp Ser Asn Tyr Asn Glu Lys Phe Arg
    50                  55                  60

Ser Lys Ala Ser Leu Thr Val Asp Lys Ser Ser Ser Thr Val Tyr Met
65                  70                  75                  80

Gln Leu Ser Ser Leu Thr Ser Glu Asp Ser Ala Val Tyr Tyr Cys Ala
                85                  90                  95

Phe Gly Tyr Phe Asp Val Trp Gly Gln Gly Thr Thr Val Thr Val Ser
            100                 105                 110

Ser

<210> SEQ ID NO 37
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 37

Asp Val Leu Met Thr Gln Thr Pro Leu Ser Leu Pro Val Ser Leu Gly
1               5                   10                  15

Asp Gln Ala Ser Ile Ser Gln Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Phe Val Pro Trp Thr Phe Gly Gly Gly Thr Lys Leu Glu Ile Lys
            100                 105                 110

Arg

<210> SEQ ID NO 38
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 38

Asp Ile Gln Met Thr Gln Ser Pro Ser Ser Met Tyr Ala Ser Leu Gly
1               5                   10                  15

Glu Arg Val Ser Ile Thr Gln Lys Ala Ser Gln Asp Ile Asn Ser Tyr
            20                  25                  30

-continued

```
Leu Ser Trp Phe Gln Gln Lys Ser Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Ser Leu Thr Ile Ser Ser Leu Glu Tyr
65              70                  75                      80

Glu Asp Met Gly Ile Tyr Tyr Cys Leu Gln Tyr Asp Glu Phe Pro Phe
            85                      90                  95

Thr Phe Gly Ser Gly Thr Lys Leu Glu Ile Lys Arg
            100             105
```

ANTIBODY AGAINST RGD IN AMINO ACID SEQUENCE OF EXTRACELLULAR MATRIX PROTEIN AND PRODUCTION METHOD AND USE OF THE SAME

CROSS-REFERENCE TO RELATED APPLICATIONS

This application is a National Stage application of PCT/JP2007/071279, filed Oct. 25, 2007, which claims priority from Japanese application JP 2006-290737, filed Oct. 26, 2006.

TECHNICAL FIELD

The present invention relates to an antibody to RGD in an amino acid sequence of an extracellular matrix protein and methods for preventing, treating and diagnosing cancer, inflammatory diseases, autoimmune diseases, infectious disease and bone disease using the antibody.

BACKGROUND ART

Cell adhesion plays an important role in sustaining life of multicellular organisms. Cell adhesions of multicellular organisms are classified into cell-extracellular matrix adhesion and cell-cell adhesion. It has been elucidated that the cell-extracellular matrix adhesion is mediated by integrins and the cell-cell adhesion is mediated by cadherins, claudins, nectins, etc. In addition, it is becoming clear that these adhesion molecules not only play a role in cell adhesion, but also are directly involved in signal transduction into cells.

Cell-extracellular matrix adhesions are consisted of transmembrane adhesion proteins such as integrins. It is reported that integrin forms heterodimer of α and β chains. There are at least 24 types of integrin molecules, which depend on the type of combination of α chain and β chain. Each type of integrin binds to a specific extracellular matrix molecule. Transmembrane adhesion proteins including integrins are involved in not only cell-extracellular matrix adhesions but also intracellular signal transductions from extracellular matrix and regulation of proliferation, mobility, apoptosis and differentiation (F. G Giancotti, et al., Science, 285, 1028-1032, 1999).

Many proteins are known as extracellular matrix molecules which are classified into collagens (such as types I to XIX), non-collagenous glycoproteins (such as osteopontin, vitronectin, fibronectin, von Willebrand Factor, laminin, tenascin, fibrinogen, thrombospondin), elastins and proteoglycans (such as heparan sulfate proteoglycan). It is appeared that these extracellular matrix molecules (ligands) bind to corresponding integrins and activate intracellular signal transduction pathways to regulate cytoskeltal organization, mobility, proliferation, differentiation and the like. That is, integrins which bind to ligands cooperate with cell-surface receptor-type tyrosine kinase to regulate these signal activating pathways by transmitting specific signals depending on the type of ligand. It is appeared that RGD (Arginine-Glycine-Asparagine acid) sequence is commonly observed in cell adhesion region of many extracellular matrix proteins. Therefore, since the RGD sequence of extracellular matrix proteins binds to integrins to exhibit various functions, the RGD sequence can be a medicinal target, and many small-molecular compounds and synthetic peptides have been provided.

As integrins which bind to the RGD sequence, α3β1 integrin, α5β1 integrin, α8β1 integrin, αvβ1 integrin, αvβ3 integrin, αvβ3 integrin, αvβ6 integrin, and αvβ8 integrin are present. Mechanisms of integrin mediated signal transduction has been studied mainly with interaction between α5β1 integrin and its specific ligand fibronectin, and it is reported that α5β1 integrin regulates not only cell adhesion and cell mobility but also cell differentiation and cell mortality (S. M. Frisch et al., Curr. Opin. Cell Biol., 9, 701-706, 1997). However, each integrin mediated signal differs depending on the type of the ligand. For example, fibronectin-bound endothelial cells show proliferation by stimulation of growth factor, but when similar cells bind to laminin-1, the growth is inhibited. Further, the signal transmitted from laminin-10/11 via α3β1 integrin is different from the signal transmitted from fibronectin via α5β1 integrin, and significantly enhances a mobility of tumor cells (J. Gu et al., J. Biol. Chem., 276, 27090-27097, 2001) and significantly avoids apoptosis by blood starvation (J. Gu et al., J. Biol. Chem., 277, 19922-19928, 2002). Among the integrins which bind to the RGD sequence, high expression of αv integrins has been observed in the osteoclast and neovascular, and the αv integrins have been expected as target molecules for a therapeutic medicine for osteoporosis and cancer. It has been indicated that α5β1 integrin are highly expressed on tumor cells and involved in malignancy of tumor cells. Based on these findings, anti-α5β3 integrin antibody (Volocimab), anti-α4 integrin antibody (Natalizumab), and anti-αvβ3 integrin antibody (Vitaxin) have been developed as antagonistic antibody medicines which inhibit binding of extracellular matrix protein to integrin.

Meanwhile, some extracellular matrix proteins such as collagen, osteopontin (OPN), vitronectin, fibronectin, von Willebrand Factor, laminin, tenascin, fibrinogen and thrombospondin have been known to include RGD sequence. Also, some virus and some bacterium have RGD sequence which is concerned in adhesion to cells. OPN, which is contained rich in bone and includes RGD sequence, is an acidic glycoprotein with binding properties to calcium which is contained rich in bone. It is reported that OPN plays an important role in cell adhesion, cell migration, tumor formation, immune response, complement mediated cellular lysis, etc. Analyses using OPN knockout mice and anti-OPN neutralizing antibodies indicate that OPN relates to hepatitis, autoimmune disease such as rheumatoid arthritis and metastasis of cancer. Therefore, it is expected that inhibition of binding of extracellular matrix proteins to cells via RGD may be used for a treatment of osteoporosis or cancer. Thus, in addition to the above mentioned antagonistic medicines targeted to integrins, antagonistic medicines targeted to the extracellular matrix proteins have been developed.

DISCLOSURE OF THE INVENTION

Small-molecular compounds and synthetic peptides that inhibit the RGD sequence-mediated interaction with integrin, antibodies against OPN and antibodies against integrin have been developed, however, there is no specific antibody to the RGD sequence. Further, since antibodies against OPN or integrin inhibit binding of extracellular matrix proteins to integrin at a sequence other than the RGD sequence, there is a possibility of generation of undesired actions in the body and generation of adverse effects.

Therefore, both efficient meritorious effects on diseases such as inflammation, cancer, infectious disease, autoimmune diseases and osteoporosis and reduction in adverse effects can be expected by specifically inhibiting the RGD sequence-mediated adhesion, and it is strongly desired to provide more advanced methods for treating these diseases.

For evaluation of effects of an antibody against human OPN or integrin using a disease model animal, such evaluation is generally carried out using an antibody from a heterologous animal against the target protein or peptide of the animal because the antibody does not crossreact with a target protein or peptide of the animal. Chimeric antibodies administered to human, humanized antibodies or human antibodies are totally different from the antibodies used for the evaluation with the disease model animal. This is a big problem in the development of pharmaceutical products. Therefore, it is desired to use an antibody to be used for treatment of human for evaluation of its therapeutic effects in the disease model animal.

In order to inhibit binding of extracellular matrix protein to integrin via the RGD sequence, the present inventors conducted extensive researches on preparation of antibodies against the RGD sequence, and as a result successfully prepared a mouse monoclonal antibody using a partial peptide of mouse OPN including the RGD sequence, and found that the antibody to the RGD sequence also crossreacts with the RGD sequence of human extracellular matrix protein and has anti-inflammatory effect, anti-cancer effect, etc., so as to complete the present invention.

Specifically, the present invention provides an anti-RGD antibody, a method for producing the anti-RGD antibody, a diagnostic/therapeutic agent for cancer, inflammatory diseases, infectious disease, autoimmune diseases or bone disease comprising the anti-RGD antibody as an active component, a method for producing a chimeric antibody, humanized antibody or human antibody of the anti-RGD antibody, etc. as described below.

(1) An anti-RGD antibody comprising any of the amino acid sequences of SEQ ID NOS: 1 to 12.
(2) An anti-RGD antibody comprising any of the amino acid sequences of SEQ ID NOS: 1, 3, 5, 7, 9 and 11.
(3) An anti-RGD antibody comprising the amino acid sequences of SEQ ID NOS: 1, 3, 5, 7, 9 and 11.
(4) An anti-RGD antibody comprising any of the amino acid sequences of SEQ ID NOS: 2, 4, 6, 8, 10 and 12.
(5) An anti-RGD antibody comprising the amino acid sequences of SEQ ID NOS: 2, 4, 6, 8, 10 and 12.
(6) The anti-RGD antibody according to any one of items (1) to (5), which comprises any of the amino acid sequences of SEQ ID NOS: 1 to 6 as an amino acid sequence in a complementary determining region of heavy chain (CDRH) and any of the amino acid sequences of SEQ ID NOS: 7 to 12 as an amino acid sequence in a complementary determining region of light chain (CDRL).
(7) The anti-RGD antibody according to any one of items (1) to (6), which specifically recognizes the RGD sequence of extracellular matrix proteins of a human and/or a mouse.
(8) The anti-RGD antibody according to any one of items (1) to (7), which is a monoclonal antibody.
(9) A monoclonal antibody which specifically recognizes the RGD sequence of extracellular matrix proteins of a human and a mouse.
(10) The anti-RGD antibody according to any one of items (1) to (9), which inhibits binding of extracellular matrix proteins of a human and/or a mouse to an RGD receptor.
(11) The anti-RGD antibody according to any one of items (1) to (10), which is a chimeric antibody.
(12) The anti-RGD antibody according to any one of items (1) to (10), which is a humanized antibody.
(13) The anti-RGD antibody according to any one of items (1) to (10), which is a human antibody.
(14) An anti-RGD monoclonal antibody produced by a hybridoma cell of Accession No. FERM BP-10440 or FERM BP-10441.
(15) A therapeutic medicine for cancer, inflammatory diseases, infectious disease, autoimmune diseases or bone disease, comprising the anti-RGD antibody according to any one of items (1) to (14) as an active component.
(16) A diagnostic medicine for cancer, inflammatory diseases, infectious disease, autoimmune diseases or bone disease, comprising the anti-RGD antibody according to any one of items (1) to (14) as an active component.
(17) A method for producing the anti-RGD antibody according to any one of items (1) to (14), wherein CVDVPNGRGD-SLAYGLR (SEQ ID NO: 13) is used as an antigen.
(18) A method for producing a chimeric antibody in which a complementary determining region of the anti-RGD antibody according to any one of items (1) to (14) is incorporated into a human antibody by means of gene engineering.
(19) A method for producing a humanized antibody in which a complementary determining region of the monoclonal antibody according to any one of items (1) to (14) is incorporated into a human antibody by means of gene engineering.
(20) A method for producing a human antibody, wherein CVDVPNGRGDSLAYGLR (SEQ ID NO: 13) is used as an antigen.

The monoclonal antibody of the present invention specifically reacts with RGD in the amino acid sequence present in extracellular matrix proteins of a mouse and a human. A part of the antibodies showed crossreactivity with osteopontin (OPN), fibronectin (FN), vitronectin (VN) and laminin, which are extracellular matrix proteins having the RGD structure. Further, since the monoclonal antibody of the present invention reacts with extracellular matrix proteins of a human and a mouse, it can be used to evaluate medicinal effects using a disease model mouse. Moreover, the monoclonal antibody of the present invention can be used for treating inflammatory diseases such as hepatitis, growth and metastasis of cancer, autoimmune diseases such as rheumatism, etc., in which the extracellular matrix protein is involved.

BRIEF DESCRIPTION OF THE DRAWINGS

FIG. 1 discloses "GRGDS" as SEQ ID NO: 24, "SLAYGLR" as SEQ ID NO: 25 and "SVVYGLR" as SEQ ID NO: 26.

FIG. 2 discloses "GRGDS" as SEQ ID NO: 24, "SLAYGLR" as SEQ ID NO: 25 and "SVVYGLR" as SEQ ID NO: 26.

FIG. 3 discloses "VDVP-NGRGDSLAYGLR" as SEQ ID NO: 27, "VDVPNGRGDS" as SEQ ID NO: 30 and "GRGDSLAYGLR" as SEQ ID NO: 31.

FIG. 4 discloses "VDVPNGRGDSLAYGLR" as SEQ ID NO: 27, "PNGRGD" as SEQ ID NO: 32 and "GDSLAYG" as SEQ ID NO: 33.

FIG. 7 discloses SEQ ID NOS 37 and 38, respectively, in order of appearance.

FIG. 12 shows the effect of anti-RGD antibodies to suppress pulmonary metastasis in experimental pulmonary metastasis model. In this Figure, A indicates the number of metastatic cells and B indicates the change of body weight.

BEST MODE FOR CARRYING OUT THE INVENTION

Figure 1:
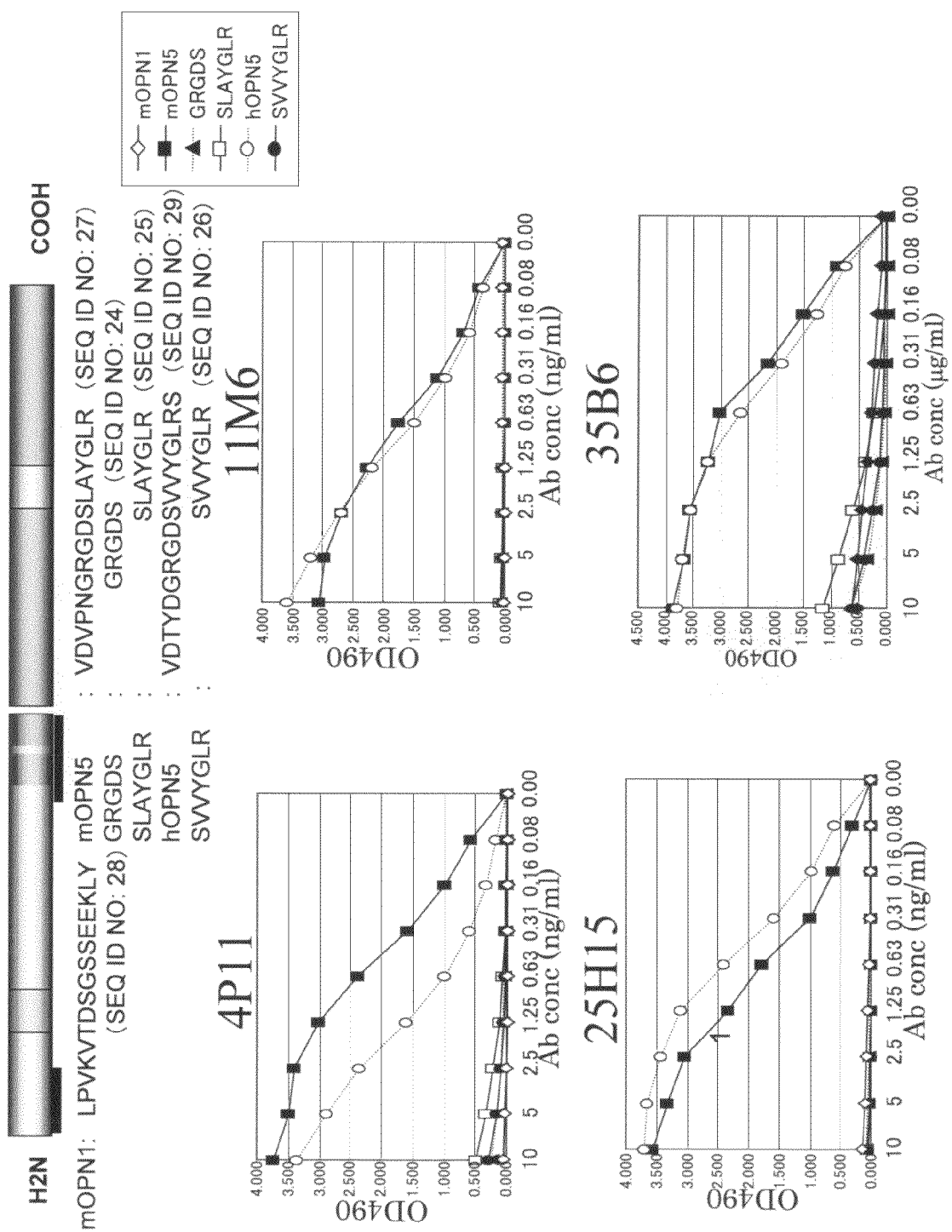
FIG. 1 shows analytical results of epitopes recognized by antibodies 4P11, 11M6, 25H15 and 35B6 using partial peptides of human OPN and murine OPN.
Figure 2:
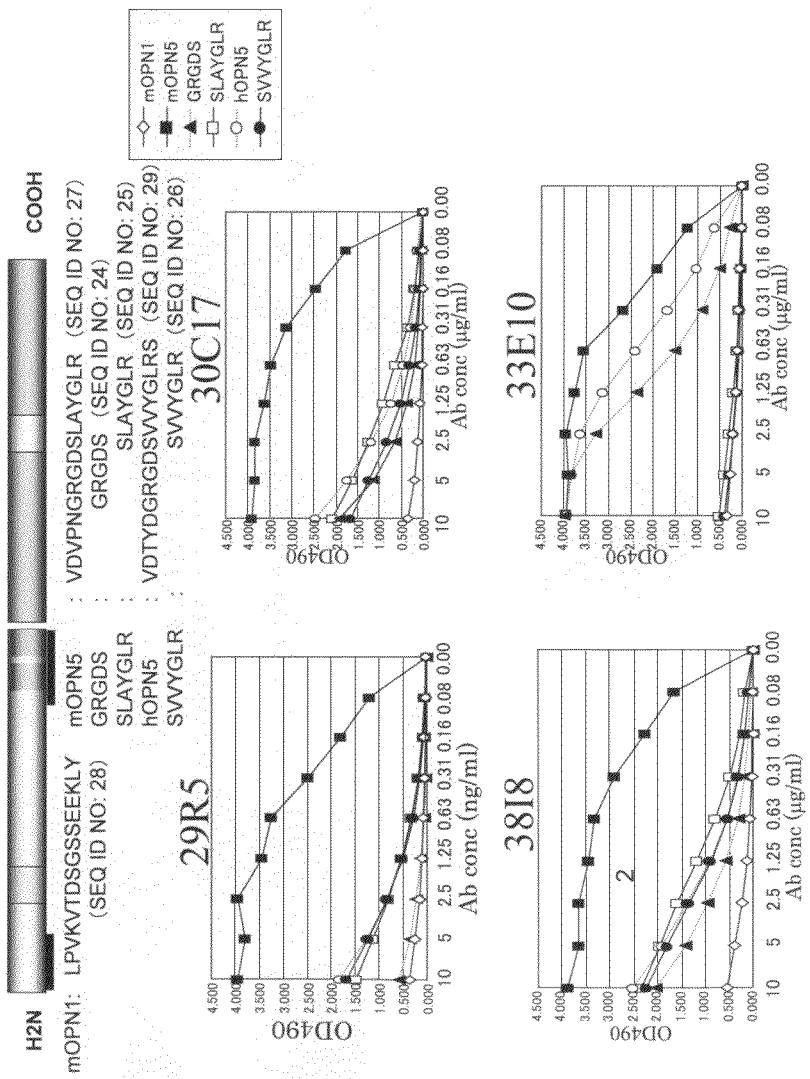
FIG. 2 shows analytical results of epitopes recognized by antibodies 29R5, 30C17, 33E10 and 38I8 using partial peptides of human OPN and murine OPN.
Figure 3:
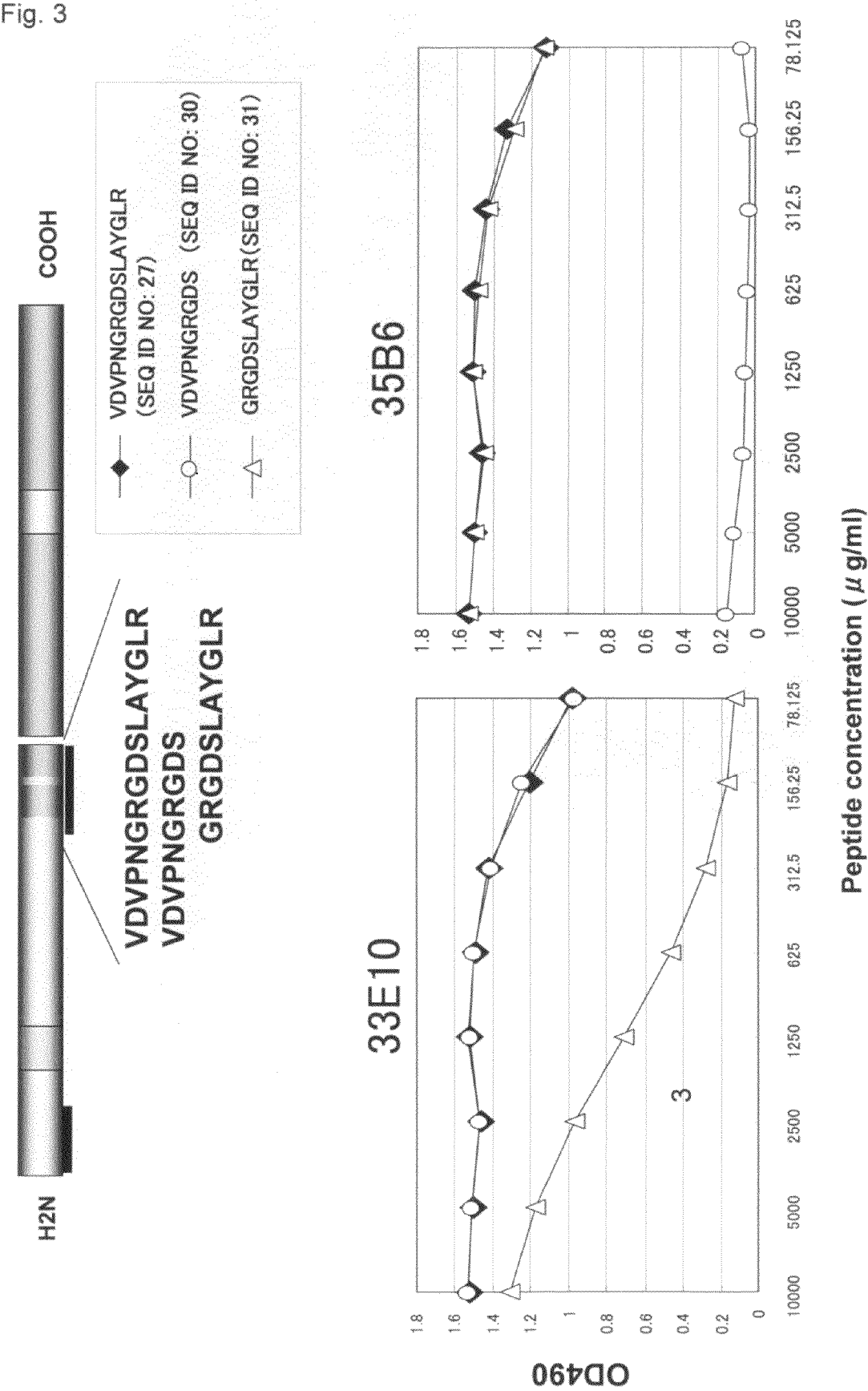
FIG. 3 shows analytical results of epitopes recognized by antibodies 33E10 and 35B6 using partial peptides of murine OPN including the RGD sequence.
Figure 4:
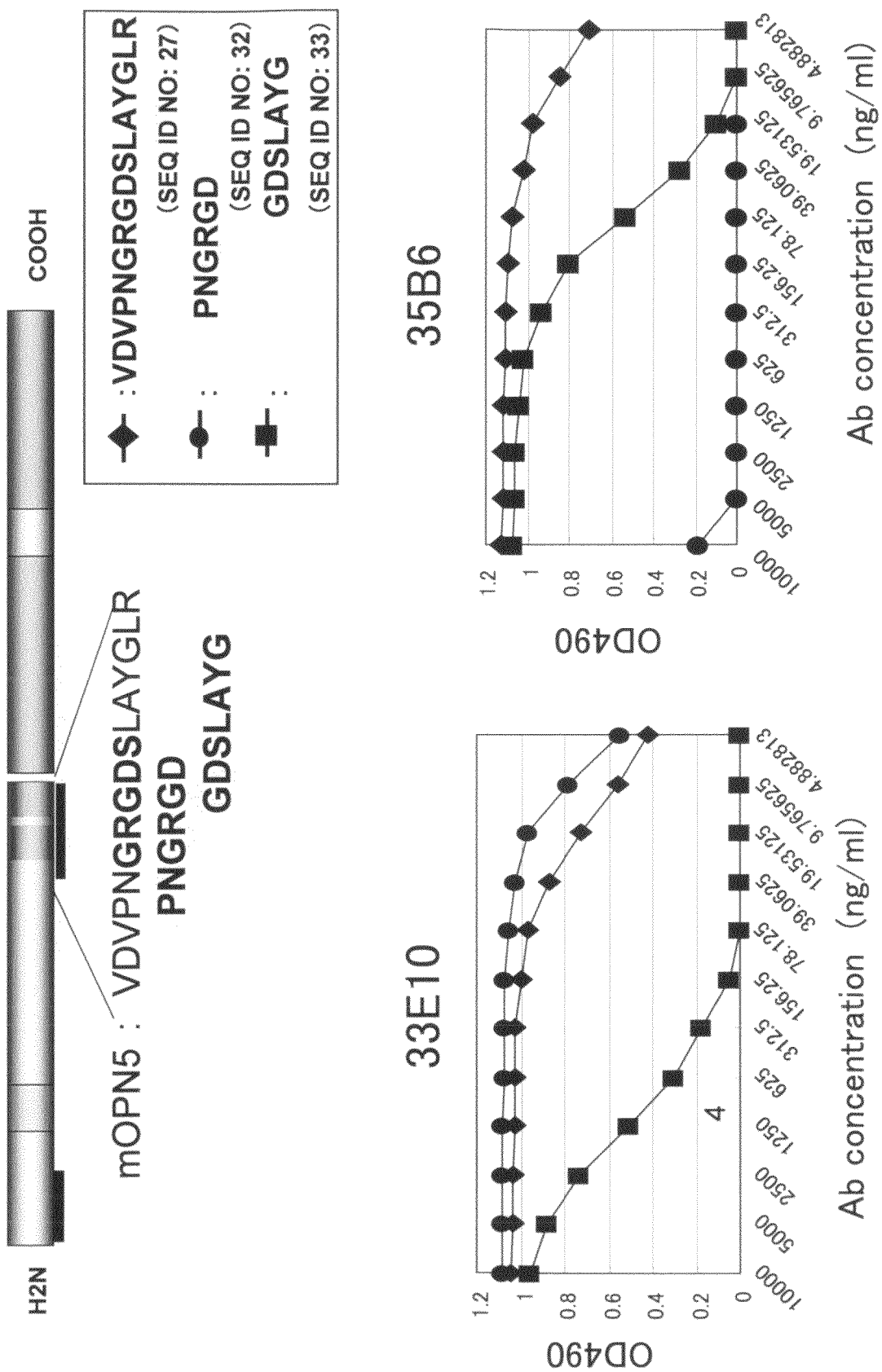
FIG. 4 shows analytical results of epitopes recognized by antibodies 33E10 and 35B6 using partial peptides of murine OPN.
Figure 5:
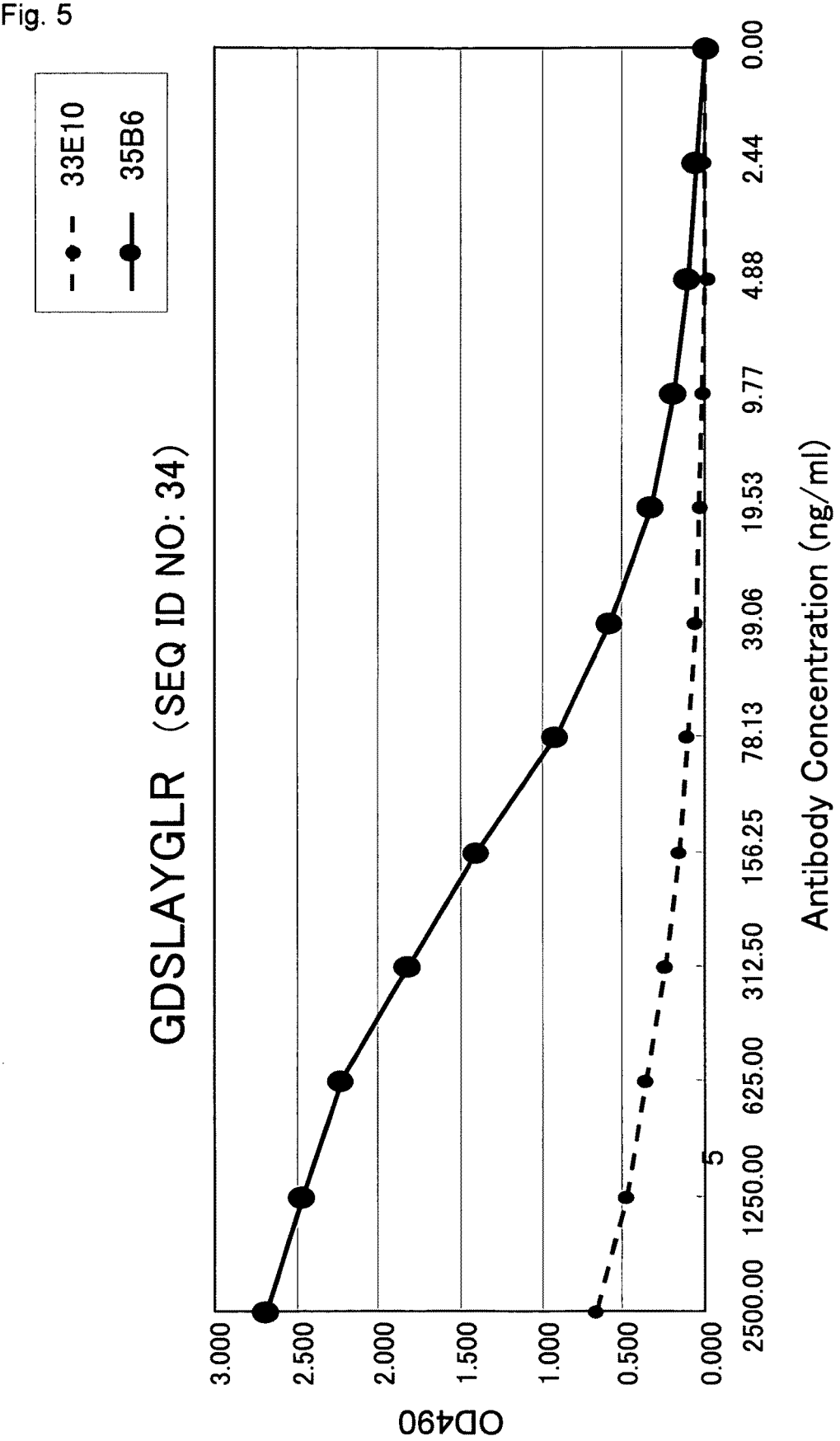
FIG. 5 shows analytical results of epitopes recognized by antibodies 33E10 and 35B6 using a partial peptide of murine OPN(CGDSLAYGLR (SEQ ID NO: 19)).

The present inventors carefully carried out the procedures described below and successfully obtained mouse monoclonal antibodies which specifically react with RGD in the amino acid sequence present in extracellular matrix proteins of a mouse and a human.

Firstly, in preparation of monoclonal antibodies to the RGD sequence, not using an amino acid sequence of human OPN, but using a partial peptide including the RGD sequence designed from mouse OPN, preparation of mouse monoclonal antibodies was tried. This was also for the purpose of evaluating medicinal effects using a disease model mouse. As a result, 8 types of mouse monoclonal antibodies were successfully prepared using partial peptide of mouse OPN. This had been generally thought impossible. It was confirmed that the obtained monoclonal antibodies recognize the RGD sequence. Moreover, it was found that the obtained monoclonal antibodies crossreact with human extracellular matrix proteins including the RGD sequence, though different monoclonal antibodies show different reactivities. It was also confirmed that these monoclonal antibodies inhibit binding between the RGD sequence and integrin.

Next, possible medicinal effects of the obtained monoclonal antibodies were evaluated using a disease model mouse. It was observed that, when the obtained monoclonal antibodies were administered to the model mouse of fulminant hepatitis which was developed by administration of ConA, indexes of hepatitis, AST and ALT were clearly decreased. Further, the cancer metastasis inhibitory effect of the obtained monoclonal antibodies was examined using experimental cancer metastasis model and spontaneous cancer metastasis model. Specifically, in the case of experimental cancer metastasis model, a mouse tumor cell B16-Luc was intravenously administered to a mouse and the number of cancer metastasis in the mouse lung was counted, and in the case of spontaneous cancer metastasis model, B16-BL6 cell was administered to a mouse in the foodpad and thereafter the number of pulmonary metastasis was counted. Thus, the cancer metastasis inhibitory effect of the obtained monoclonal antibodies was examined. As a result, in both the models, the obtained monoclonal antibodies exerted a cancer metastasis inhibitory effect. In addition, it was confirmed that the obtained monoclonal antibodies showed clear effect in treating rheumatoid arthritis in a rheumatoid model mouse which was developed by administration of cocktail of Type II collagen antibody and LPS.

1. Anti-RGD Antibody of the Present Invention

The present invention provides a monoclonal antibody to the RGD sequence. More specifically, the present invention provides a monoclonal antibody which specifically recognizes the amino acid sequence RGD of extracellular matrix proteins of a human and a mouse.

As used herein, the term "extracellular matrix protein" refers to a protein which constitutes an extracellular matrix. Examples thereof include, but are not limited to, osteopontin, vitronectin, fibronectin, von Willebrand Factor, collagen, laminin, tenascin, fibrinogen, thrombospondin, angiostatin, plasmin, and VCAM-1. As used herein, the term "extracellular matrix" refers to a complex aggregate of biological polymers, which fills the extracellular space in tissue, in accordance with the meaning commonly used in the art (for example, see "Dictionary of Molecular Cell Biology", page 323, Tokyo Kagaku Dozin Co., Ltd., 1997). As used herein, the term "extracellular matrix protein" is interchangeable with the term "extracellular matrix molecule".

As used herein, the term "antibody" refers to a whole antibody molecule or a fragment thereof (e.g., fragments such as Fab, Fab', and F(ab')$_2$), and it may be a polyclonal or monoclonal antibody. Preferably, the antibody of the present invention is a monoclonal antibody. Further, in the present invention, the "antibody" includes chimeric antibody, humanized antibody and human antibody.

In the specification, when an antibody "specifically recognizes" a protein or a fragment thereof, it means that the antibody binds to a specific amino acid sequence of the protein or the fragment thereof with affinity which is substantially higher than affinity to other amino acid sequences. In this regard, "affinity which is substantially higher" means affinity that is high enough to enable detection of a specific amino acid sequence which is distinguished from other amino acid sequences using a desired measurement apparatus. Typically, it means binding affinity having a binding constant ($K_a$) of at least $10^7$ M$^{-1}$, preferably at least $10^8$ M$^{-1}$, more preferably $10^9$ M$^{-1}$, and even more preferably $10^{10}$ M$^{-1}$, $10^{11}$ M$^{-1}$, M$^{-1}$ or higher (e.g., up to $10^{13}$ M$^{-1}$ or higher).

As used herein, the term "anti-RGD antibody" refers to an antibody which specifically recognizes the RGD sequence in a protein, polypeptide or peptide.

As used herein, the term "monoclonal antibody" refers to an antibody which is obtained from a substantially-homogeneous population of antibodies, i.e., a population of antibodies in which antibodies constituting the population are homogeneous except for a small amount of mutants which may naturally occur. A monoclonal antibody is highly specific and provides action on a single antigenic site. Moreover, compared to a polyclonal antibody, which includes different antibodies to different epitopes, each monoclonal antibody is directed to a single epitope on an antigen. In addition to its specificity, the monoclonal antibody is advantageous on the point that homogeneous antibodies can be constantly produced by means of culture of hybridoma in which no other immunoglobulin is mixed and purification can be more easily carried out. The modifying word "monoclonal" suggests properties of antibodies obtained from a substantially-homogeneous population of antibodies, and does not limit a method of producing antibodies to a specific method.

As used herein, the term "antibody fragment" refers to a portion of a full-length antibody, and it means an antigen binding region or a variable region. Examples of antibody fragments include Fab, Fab', F(ab')$_2$ and a Fv fragment. These antibody fragments can be prepared using a generally-known method such as papain digestion and pepsin digestion of antibody.

The term "chimeric antibody" refers to a chimeric human/murine antibody in which the constant region of the anti-RGD antibody obtained in the present invention is genetically modified so as to have the same constant region as a human antibody (see EP Laid-Open Publication No. 0125023). The term "humanized antibody" refers to an antibody in which the primary structure of the anti-RGD antibody obtained in the present invention, except for the complementary determining regions of H-chain and L-chain, is genetically modified to provide a primary structure corresponding to a human antibody. The term "human antibody" refers to a monoclonal antibody which is prepared using a transgenic animal in which a human gene involved in antibody production is introduced (see EP Laid-Open Publication No. 0546073).

In the present invention, particularly preferred antibodies are anti-RGD antibodies produced by hybridoma cells of Accession Nos. FERM BP-10440 and FERM BP-10441 indicated in the Examples in the specification.

Hereinafter, preparation of anti-RGD monoclonal antibody will be described in detail, but the method for preparing an antibody is not limited thereto.

2. RGD Sequence-Containing Peptide (Antigen)

Examples of RGD sequence-containing peptides to be used as antigens in the present invention include peptides consisting of an amino acid sequence, which comprises at least the "RGD" sequence as a cell adhesion sequence, and which can produce an antibody to the RGD sequence by immunization, such as the amino acid sequence CVDVPNG RGDSLAYGLR (SEQ ID NO: 13) comprising the RGD sequence which is a cell adhesion sequence of extracellular matrix protein of a mouse used in the Examples.

Examples of "RGD sequence-containing peptide", "peptide which contains the RGD sequence" or "peptide consisting of an amino acid sequence including the RGD sequence" include RGD sequence-containing peptides such as osteopontin (OPN), vitronectin, fibronectin, von Willebrand Factor, collagen, laminin, tenascin, fibrinogen and thrombospondin, which are known as extracellular matrix protein containing the RGD sequence. Further, the "RGD sequence-containing peptide", "peptide which contains the RGD sequence" or "peptide consisting of an amino acid sequence including the RGD sequence" in the present invention is an amino acid sequence consisting of at least about 5 amino acids, preferably about 5 to 50 amino acids, and more preferably about 10 to 20 amino acids. In the specification, the term "RGD sequence-containing peptide" is interchangeable with "peptide which contains the RGD sequence" or "peptide consisting of an amino acid sequence including the RGD sequence".

In this regard, the "RGD sequence-containing peptide" or "peptide consisting of an amino acid sequence including the RGD sequence" to be used in the present invention also includes a variant polypeptide comprising an amino acid sequence in which a plurality of amino acids, preferably 1 to 10 amino acids, and particularly preferably 1 to several (e.g., 1 to 5) amino acids in the above-described amino acid sequence are substituted, deleted, and/or modified, or a variant polypeptide comprising an amino acid sequence in which a plurality of amino acids, preferably 1 to 10 amino acids, and particularly preferably 1 to several (e.g., 1 to 5) amino acids in the above-described amino acid sequence are added or inserted, as long as such variant polypeptides have substantially-equivalent antigenicity. Moreover, the "RGD sequence-containing peptide" or "peptide consisting of an amino acid sequence including the RGD sequence" may be a variant polypeptide having a plurality of such substitutions, deletions, modifications, additions and insertions.

The peptide consisting of an amino acid sequence comprising the RGD sequence to be used in the present invention can be produced by suitably employing methods publicly known in the art, such as a chemical synthesis method, gene recombinant method and cell culture method, or modification thereof. The peptide can be produced by suitably cleaving an isolated extracellular matrix protein using protease or the like. Further, the peptide consisting of an amino acid sequence including the RGD sequence may be derived from a mammal such as mouse, rat, human, swine, monkey, bovine and rabbit. As long as the RGD sequence-containing peptide can produce an antibody to the RGD sequence, the method of producing the peptide is not particularly limited.

To the above-described RGD sequence-containing peptide, other biological polymers may be bound in order to further enhance antigenicity thereof. Examples of such biological polymers to enhance antigenicity include thyroglobulin, keyhole limpet haemocyanin (KLH), bovine serum albumin (BSA), ovalbumin (OVA) and bovine globulin, and thyroglobulin is more preferred. Further, examples of methods for binding the peptide including the RGD sequence to a biological polymer include coupling reagent method (a binding reagent having active ester group and maleimide functional group: the active ester group binds to amino group of a protein or peptide and the maleimide group binds to SH group of a protein or peptide) (S. Yoshitake et al., Eur. J. Biochem., 101, 395-399, 1979), mixed anhydride method (B. F. Erlanger et al., J. Biol. Chem., 234, 1090-1094, 1954), and active ester method (A. E. Karu et al., J. Agric. Food Chem., 42, 301-309, 1994). The coupling reagent method is preferred.

3. Preparation of Antibody-Producing Cell

An antigen per se is administered solely or in combination with a carrier and a diluent to an animal to be immunized at a region where antibodies can be produced by the administration. At the time of the administration, a complete Freund's adjuvant or incomplete Freund's adjuvant may be administered in order to enhance antibody-producing ability. The administration is generally carried out about 2 to 10 times (every 1 to 6 weeks). Examples of warm-blooded animals to be used include mouse, monkey, rabbit, dog, guinea pig, rat, hamster, sheep, goat, chicken, etc. In the present invention, mouse is preferably used.

If a subject to be treated is human and an animal which produces the anti-RGD antibody is mouse, then a human-mouse chimeric antibody or a humanized antibody is desirably used. More desirably, a human-type monoclonal antibody is used, which is prepared utilizing a transgenic animal such as a mouse into which a human gene involved in antibody production is introduced.

4. Cell Fusion Between Antibody Producing Cell and Myeloma Cell

As a myeloma cell, a cell from mouse, rat, human or the like is used. Examples thereof include mouse myelomas P3U1, P3X63-Ag8, P3X63-Ag8-U1, P3NS1-Ag4, SP2/0-Ag14, P3X63-Ag8-653, etc. It is preferred that an antibody producing cell and a myeloma cell are derived from animals of the same species, in particular, of the same strain. A myeloma cell can be frozen for preservation or maintained by subculture in a general medium to which bovine fetal serum is added. It is preferred that a cell in the logarithmic growth phase is used for cell fusion. In the present invention, P3X63-Ag8-653 is preferably used.

Examples of methods for forming a hybridoma by fusing an antibody producing cell and a myeloma cell include a method using polyethylene glycol (PEG), a method using Sendai virus, and a method using an electrofusion apparatus. For example, in the case of the PEG method, splenic cells and myeloma cells may be suspended in a suitable medium or buffer solution containing about 30 to 60% PEG (average molecular weight: 1000 to 6000) in the mixing ratio of 1 to 10:1, preferably 5 to 10:1 to cause a reaction at about 25 to 37° C. at pH 6 to 8 for about 30 seconds to 5 minutes. After the reaction is completed, PEG solution is removed, resuspension is performed in the medium, and seeding is carried out in a cell well plate to continue culturing.

5. Selection of Hybridoma Cell

Selection of a hybridoma cell which produces a monoclonal antibody can be carried out according to a publicly-known method or a method corresponding thereto. Generally, it can be carried out in a medium for animal cells to which HAT (hypoxanthine, aminopterin, thymidine) is added. As a medium for selection and breeding, any medium can be used as long as hybridoma cells can be grown therein. Examples of such mediums include: RPMI 1640 medium containing 1 to 20%, preferably 10 to 20% bovine fetal serum; GIT medium containing 1 to 10% bovine fetal serum (Wako Pure Chemical Industries, Ltd.); and serum-free medium for hybridoma culture (SFM-101, Nissui Pharmaceutical Co., Ltd.). Culture temperature is generally 20 to 40° C., and preferably about 37° C. Culture time is generally 5 days to 3 weeks, and preferably 1 to 2 weeks. Culture can be generally performed under 5% $CO_2$.

Production of the monoclonal antibody of the present invention can be confirmed and subjected to screening using the ELISA method described in "Rinpa-kyu Kinou Tansaku-Hou (Method for detecting lymphocyte function)" (written and edited by Junichi Yada and Michio Fujiwara, Chugai-Igakusha, pages 588-592, 1994). A clone which had a positive reaction by ELISA may be repeatedly subjected to the limiting dilution once to 5 times, and preferably 2 to 4 times to prepare a monoclonal antibody. In order to obtain clones which react with the RGD sequence from various hybridomas obtained by cell fusion, hybridomas which produce antibodies recognizing the RGD sequence may be screened using the ELISA method in which a peptide including the RGD sequence as an antigen, for example, CVDVPNGRGD-SLAYGLR (SEQ ID NO: 13) is immobilized on a 96-well plate, reacted with culture supernatant of hybridomas, and thereafter detection is carried out using an enzyme-labeled anti-mouse IgG antibody.

6. Separation/Purification of Antibody

Antibodies obtained can be homogeneously purified. In order to separate/purify antibodies, a separation/purification method generally used for proteins may be used. For example, by suitably selecting and combining things such as a chromatography column of gel filtration, ion-exchange chromatography, affinity chromatography or the like, a filter, ultrafiltration, salting-out, dialysis, SDS polyacrylamide gel electrophoresis, isoelectric focusing electrophoresis, etc., antibodies can be separated and purified (Antibodies: A Laboratory Manual. Ed Harlow and David Lane, Cold Spring Harbor Laboratory, 1988), but the present invention is not limited thereto. Examples of carriers to be used in affinity chromatography include antigen binding resin, protein A binding resin and protein G binding resin. Examples of antigen binding resins include thiol-sepharose beads (Amersham Biosciences). It is preferred to employ affinity chromatography using such a carrier to which a peptide including the RGD sequence as an antigen, for example, CVDVPNGRGD-SLAYGLR (SEQ ID NO: 13) binds.

7. Formulation of Antibody

The monoclonal antibody obtained in this way may be subjected to drug preparation according to the ordinary method to be used as a prophylactic and/or therapeutic medicine for cancer, inflammatory disease, infection disease, autoimmune disease, bone disease or the like. Regarding the dosage form of the prophylactic and/or therapeutic medicine, parenteral formulation such as an injectable solution and an agent for intravenous drip can be employed, and based on original ideas, the monoclonal antibody can be used in the form of oral formulation. At the time of drug preparation, a carrier, a diluent, an additive or the like, which is suitable for a formulation, can be used within the range which is pharmacologically and pharmaceutically acceptable.

A pharmaceutical preparation containing the monoclonal antibody of the present invention as an active component can be used as a prophylactic and/or therapeutic medicine for cancer (e.g., proliferation and metastasis of tumor cells), inflammatory disease (e.g., osteoarthritis, hepatitis, bronchial asthma, fibrosis, diabetes, arteriosclerosis, multiple sclerosis, and inflammatory bowel disease (ulcerative colitis, Crohn's disease)), infection disease (e.g., hepatitis), autoimmune disease (e.g., rheumatoid arthritis, systemic lupus erythematosus, polymyositis, autoimmune thyroid disease, tubulointerstitial nephritis, and myasthenia gravis), bone disease (e.g., osteoporosis) or the like.

The dose varies depending on a subject to be administered, a target disease, symptoms, a route of administration, etc. For example, in the case of use for prophylaxis and/or therapy of cancer, in general, the antibody of the present invention in an amount of about 0.01 to 20 mg/kg body weight, preferably about 0.1 to 10 mg/kg body weight, and more preferably about 0.1 to 5 mg/kg body weight for a dose is advantageously administered by means of intravenous injection about 1 to 10 times per month, and preferably about 1 to 5 times per month. In the case of other parenteral administrations and oral administrations, an amount corresponding thereto can be administered. In the case of particularly severe symptoms, the dose or the number of doses may be increased according to need.

The antibody of the present invention per se can be administered, and further, the antibody in the form of a suitable pharmaceutical composition can also be administered. The pharmaceutical composition to be used for administration comprises: the above-described antibody or a salt thereof; and a pharmacologically acceptable carrier, diluent or excipient. The composition is provided in a formulation suitable for parenteral administration or oral administration.

That is, examples of formulations for parenteral administration include an injection product, a nasal preparation, a suppository and the like, and the injection product includes formulations such as an intravenous injection product, a subcutaneous injection product, an intradermal injection product, an intramuscular injection product, a drip injection product, etc. These injection products can be prepared according to a publicly-known method, for example, by dissolving, suspending or emulsifying the above-described antibody or a salt thereof in a sterile aqueous or oily solution generally used for an injection product. Examples of aqueous solutions for injection include saline, an isotonic solution containing other adjuvants such as glucose, saccharose and mannitol, etc., and it can be used in combination with a suitable solubilization agent such as alcohol (e.g., ethanol), polyalcohol (e.g., propylene glycol, polyethylene glycol), a nonionic surfactant (e.g., Polysorbate 80, Polysorbate 20, HCO-50 (polyoxyethylene (50 mol) adduct of hydrogenated castor oil)), etc. Examples of oily solutions include sesame oil and soybean oil, and it can be used in combination with a solubilization agent such as benzyl benzoate and benzyl alcohol. The prepared injection solution is generally put into a suitable ampule, vial or syringe. A nasal preparation or suppository can be prepared by mixing the above-described antibody with a general base for nasal preparation or suppository. It is thought that it is generally difficult to perform oral administration of protein such as an antibody because of breakdown in the digestive system. However, there is a possibility of oral administration depending on application of original ideas to an antibody fragment or modified antibody fragment and a formulation.

The above-described pharmaceutical composition for parenteral administration is preferably prepared to provide a formulation having an administration unit which is suitable for the administration amount of the active component. Examples of formulations having such an administration unit include an injection product (ampule, vial, and prefilled syringe), a nasal preparation, a suppository and the like. In general, each of the administration units preferably contains the above-described antibody in an amount of 5 to 500 mg, in particular 5 to 100 mg in the case of injection products, and 10 to 250 mg in the case of other formulations.

Each of the aforementioned compositions may contain other active components as long as no undesirable interaction is generated by blending them with the above-described antibody.

8. Diagnostic Medicine Containing the Monoclonal Antibody of the Present Invention The monoclonal antibody of the present invention can be used as a diagnostic medicine for inflammatory diseases such as rheumatoid arthritis, hepatitis, bronchial asthma, fibrosis, diabetes, cancer metastasis, arteriosclerosis, multiple sclerosis, granuloma, etc., or a diagnostic medicine for chronic rejection suppression after organ transplantation and autoimmune diseases such as systemic autoimmune diseases, erythematosus, uveitis, Behcet's disease, polymyositis, proliferative glomerulonephritis, sarcoidosis, etc. Since the monoclonal antibody of the present invention can specifically recognize the RGD sequence, it can be used for quantification of extracellular matrix protein in a test solution using sandwich immunoassay, competition immunoassay, an immunometric method, a nephrometry method or the like. When applying each of these immunological measurement methods to the measurement method of the present invention, no particular condition or operation is required. The measurement system of the present invention can be established by adding a technical arrangement generally considered by those skilled in the art to general conditions and operation methods of each of these methods. Detailed information about these general technical means is described in review articles and authoritative books.

Thus, by using the antibody of the present invention, extracellular matrix protein can be highly-sensitively quantified. Moreover, by utilizing the method of quantification of extracellular matrix protein in vivo using the antibody of the present invention, various diseases associated with extracellular matrix protein can be diagnosed. For example, when increase/decrease of the concentration of extracellular matrix protein is detected, it can be diagnosed that there is a high possibility that there is a disease associated with extracellular matrix protein such as inflammatory disease, or that there is a high possibility of being affected with such a disease in future. Moreover, the monoclonal antibody of the present invention can be used in order to specifically detect the RGD sequence of extracellular matrix protein present in a test analyte such as body fluid and tissue. Furthermore, the monoclonal antibody can be used in preparation of an antibody column to be used for purifying extracellular matrix protein, detection of extracellular matrix protein contained in each fraction at the time of purification, analysis of behavior of extracellular matrix protein in a test cell, etc.

Hereinafter, the present invention will be described in more detail based on Examples, but the present invention is not limited thereto.

EXAMPLES

Example 1

Method for Preparing Antibody

The sequence CVDVPNGRGDSLAYGLR (SEQ ID NO: 13) including the RGD sequence which is the cell adhesion sequence of extracellular matrix protein and the sequence SLAYGLR (SEQ ID NO: 25) was synthesized to be combined with thyroglobulin (Sigma) via EMCS (Dojin), and a mouse was immunized with this as an immunogen together with adjuvant. After immunization was performed 4 times, splenic cell was collected to be subjected to cell fusion with myeloma cell X63-Ag8-653. After selection using a HAT medium, culture supernatant was screened using the ELISA method in which antigen peptide was immobilized to select hybridomas which produce antibodies recognizing the RGD sequence (8 clones: 4P11, 11M6, 25H15, 29R5, 30C17, 33E10, 35B6, 3818). An antigen peptide column was prepared using thiol sepharose beads (Amasham Bioscience), and antibodies were purified from supernatant of hybridomas.

The obtained hybridoma cells 33E10 and 35B6 were deposited to International Patent Organism Depositary, National Institute of Advanced Industrial Science and Technology (Chuo 6, Higashi 1-1-1, Tsukuba-shi, Ibaraki 305-8566) on Oct. 27, 2005 (Accession Nos. FERM BP-10440 and FERM BP-10441, respectively).

Example 2

Analysis of Epitope

[Peptides Used for Analysis]
mOPN1 (CLPVKTDSGSSEEKLY (SEQ ID NO: 14)), mOPN5 (CVDVPNGRGDSLAYGLR (SEQ ID NO: 13)), CVDVPNGRGDS (SEQ ID NO: 15), CPNGRGD (SEQ ID NO: 16), CGRGDSLAYGLR (SEQ ID NO: 17), CGDSLAYG (SEQ ID NO: 18), CGDSLAYGLR (SEQ ID NO: 19) and CSLAYGLR (SEQ ID NO: 20), which comprise a partial peptide derived from synthesized mouse OPN; hOPN5 (CVDTYDGRGDSVVYGLRS (SEQ ID NO: 21)) and CSVVYGLR (SEQ ID NO: 22), which are partial peptides derived from human OPN; and CGRGDS (SEQ ID NO: 23), which comprises a partial peptide common to a mouse and a human, were combined with BSA (Sigma) via EMCS (Dojin), and used as peptides for ELISA analysis.

[ELISA Method]

Peptides (10 µg/ml) or proteins (5 µg/ml) were left on a 96-well plate at 37° C. for 1 hour to be immobilized. After blocking with 0.1% BSA/PBS/0.05% NaN₃ solution, antibodies were reacted at various concentrations at 37° C. for 1 hour. Next, the plate was reacted with HRP-labeled anti-murine IgG antibody (Jackson ImmunoResearch Laboratories, Inc.) as secondary antibody at 37° C. for 30 minutes, OPD was added for coloring for 15 minutes, and 1N H₂SO₄ was added to stop the reaction, and then absorbance at 490 nm was measured.

[Epitope Mapping]

ELISA was carried out using 96-well plates to which the thyroglobulin-bound peptides synthesized were immobilized respectively.

As shown in FIG. 1, FIG. 2, FIG. 3, FIG. 4 and FIG. 5, monoclonal antibodies 4P11, 11M6, 25H5, 35B6 and 33E10 bound to mOPN5 and hOPN5, indicating that these monoclonal antibodies recognize murine and human partial peptides. In these antibodies, 33E10 did not react with CSLAYGLR (SEQ ID NO: 20) or CSVVYGLR (SEQ ID NO: 22) which includes a sequence following the RGD sequence, but reacted with CGRGDS (SEQ ID NO: 23), CVDVPNGRGDS (SEQ ID NO: 15) and CPNGRGD (SEQ ID NO: 16). It indicates that the antibody recognizes the RGD sequence, which is a sequence common to these peptides, and shows reactivity with both murine and human peptides. The monoclonal antibody 35B6 did not react with CGRGDS (SEQ ID NO: 23), CVDVPNGRGDS (SEQ ID NO: 15) or CPNGRGD (SEQ ID NO: 16), but reacted with CGRGD-SLAYGLR (SEQ ID NO: 17), CGDSLAYG (SEQ ID NO: 18) and CGDSLAYGLR (SEQ ID NO: 19). It suggests that the antibody also recognizes a sequence following the RGD sequence which comprises GD of the RGD sequence. The antibodies 29R5, 30C17 and 3818 were slightly reactive with GRGDS (SEQ ID NO: 24), SLAYGLR (SEQ ID NO: 25) or SVVYGLR (SEQ ID NO: 26), but only reacted with mOPN5. It indicates that the antibodies recognize VDVPNGRGD-SLAYGLR (SEQ ID NO: 27) of murine OPN.

Example 3

Analysis of Amino Acid Sequences of Antibodies

RNAs were extracted from hybridoma cells using RNeasy Mini kit (Qiagen), and cDNAs were prepared using First-strand cDNA synthesis kit (Amasham Bioscience). Heavy chain cDNA of the antibody was extended by PCR using Heavy primer amplification kit (Amasham Bioscience), and it was incorporated into pCRII-TOPO vector (invitrogen), and then the cDNA sequence and the amino acid sequence were determined. The CDR region was determined by ABG: Directory of 3D structures of antibodies (www.ibt.unam.mx/vir/structure/structures.html) and blast for Ig sequence (www.ncbi.nlm.nih.gov/igblast).

Figure 6:
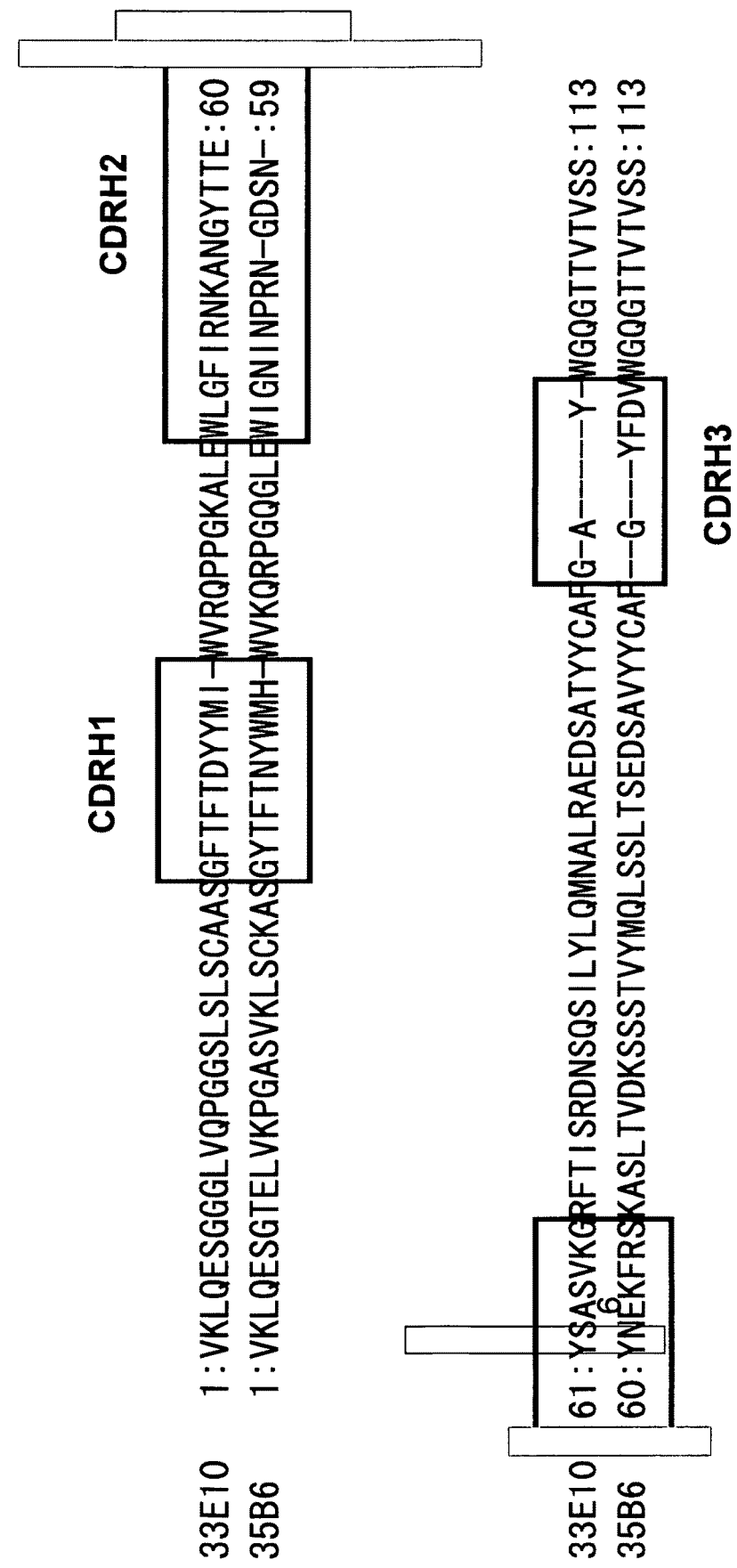
FIG. 6 shows analytical results of complementary determining region (CDR) of heavy chain of anti-RGD antibody. In both the sequences of heavy chains of 33E10 and 35B6, the first amino acid is not shown (starting from the second amino acid residue). Further, the 99th residue (F) in the sequence of 33E10 (SEQ ID NO: 35) and the 98th residue (F) in the sequence of 35B6 (SEQ ID NO: 36) may be K or R.
Figure 7:
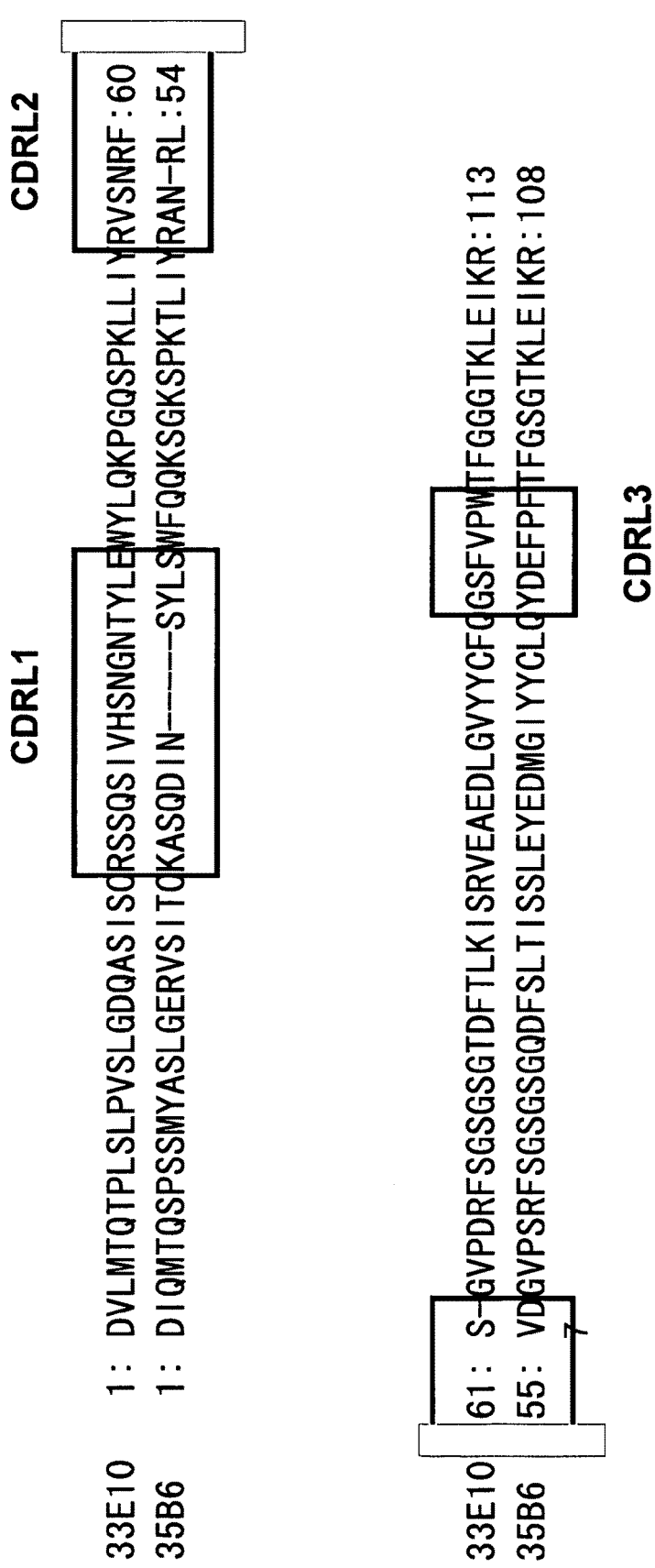
FIG. 7 shows analytical results of complementary determining region (CDR) of light chain of anti-RGD antibody.

As a result, the variable regions and CDR regions of heavy chain and light chain are the following amino acid sequences (also shown in FIG. 6 and FIG. 7):

```
(Heavy chain)
[CDRH1]
33E10:   GFTFTDYYMI           (SEQ ID NO: 1)

35B6:    GYTFTNYWMH           (SEQ ID NO: 2)

[CDRH2]
33E10:   WLGFIRNKANGYTTEYSASVKG (SEQ ID NO: 3)

35B6:    WIGNINPRNGDSNYNEKFRS  (SEQ ID NO: 4)

[CDRH3]
33E10:   GAY                  (SEQ ID NO: 5)

35B6:    GYFDV                (SEQ ID NO: 6)

(Light chain)
[CDRL1]
33E10:   RSSQSIVHSNGNTYLE     (SEQ ID NO: 7)

35B6:    KASQDINSYLS          (SEQ ID NO: 8)

[CDRL2]
33E10:   RVSNRFS              (SEQ ID NO: 9)

35B6:    RANRLVD              (SEQ ID NO: 10)

[CDRL3]
33E10:   GSFVPW               (SEQ ID NO: 11)

35B6:    YDEFPF               (SEQ ID NO: 12)
```

In this experiment, CDR regions were determined by ABG, however it can be understood by those skilled in the art that other software programs may be used for determining the CDR regions and may result in different sequences to some extent.

Example 4

Binding to Extracellular Matrix Protein Having the RGD Sequence

[Proteins Used for Analysis]

Each of human osteopontin (hOPN) and murine osteopontin (mOPN) was purified from culture supernatant of CHO-K1 cells into which each gene thereof was introduced using an anti-OPN antibody column. Human vitronectin (VN) was obtained from AGC TECHNO GLASS Co., Ltd. Human fibronectin (FN), human thrombospondin and murine laminin were obtained from Sigma Corporation.

[ELISA Method]

Peptides (10 µg/ml) or proteins (5 µg/ml) were left on a 96-well plate at 37° C. for 1 hour to be immobilized. After blocking with 0.1% BSA/PBS/0.05% NaN₃ solution, antibodies were reacted at various concentrations at 37° C. for 1 hour. Next, the plate was reacted with HRP-labeled anti-murine IgG antibody (Jackson ImmunoResearch Laboratories, Inc.) as secondary antibody at 37° C. for 30 minutes, OPD was added for coloring for 15 minutes, and 1N H₂SO₄ was added to stop the reaction, and then absorbance at 490 nm was measured.

[Binding Ability to Extracellular Matrix]

ELISA was performed using 96-well plates to which hOPN, mOPN, FN, VN or laminin was immobilized.

Figure 8:
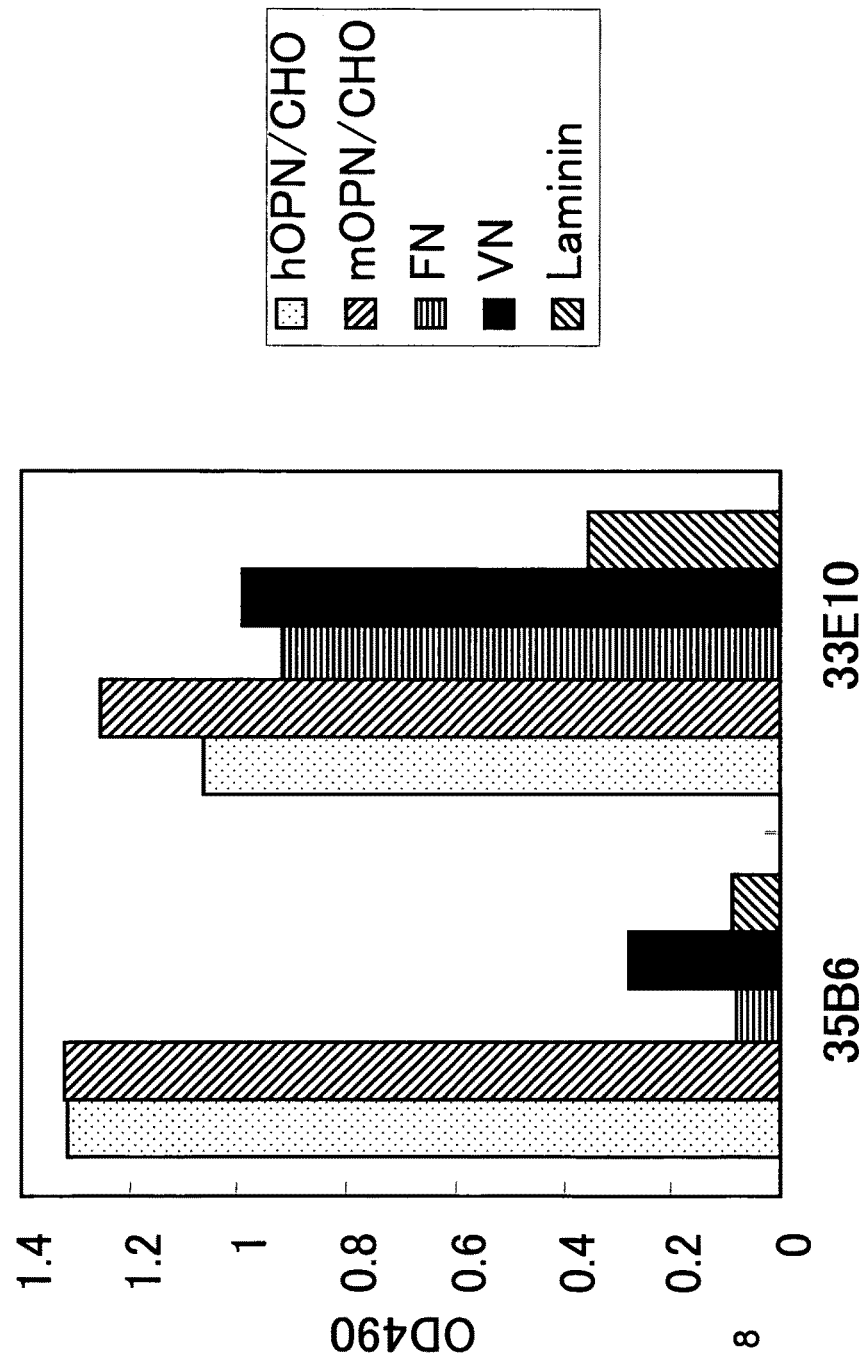
FIG. 8 shows results of binding between anti-RGD antibodies and various extracellular matrix proteins including the RGD sequence.

Results are shown in FIG. 8. The monoclonal antibody 33E10 showed low reactivity with laminin, but it is indicated that the antibody cross-reacts with all the tested extracellular matrix proteins. It was found that the monoclonal antibody 35B6 reacts with hOPN and mOPN, but not with FN, VN and laminin.

Example 5

Cell Adhesion Test

[Proteins Used for Analysis]

Each of human osteopontin (hOPN) and murine osteopontin (mOPN) was purified from culture supernatant of CHO-K1 cells into which each gene thereof was introduced using an anti-OPN antibody column. mOPN N-half was purified from $E.\ coli$ using the N-terminus of thrombin cleavage site of murine OPN as GST fusion protein. Human fibronectin (FN) and human vitronectin (VN) were obtained from Sigma Corporation.

[Method of Cell Adhesion Test]

50 μl of the proteins was added to each well of 96-well plate, and allowed to stand at 37° C. for 1 hour to be immobilized. After blocking the plate with a blocking solution (0.5% BSA/PBS) and washing with PBS once, the NIH3T3 cells suspended in 0.25% BSA-added D-MEM and monoclonal antibodies were mixed at final concentration of 1.0× $10^5$ cells/ml, and added to the plate at 200 μl/well. After reaction was performed under 5% $CO_2$ at 37° C. for 1 hour, 50 μl of 0.5% Crystal Violet (WAKO, Osaka, Japan)/20% methanol solution was added to each well of the plate, and left at room temperature for 30 minutes, thereby immobilizing and staining the cells. The plate was washed with distilled water and 20% acetic acid solution was added thereto to effect dissolution. Then, absorbance at 590 nm was measured.

[Cell Adhesion Inhibition Activity]

Figure 9:
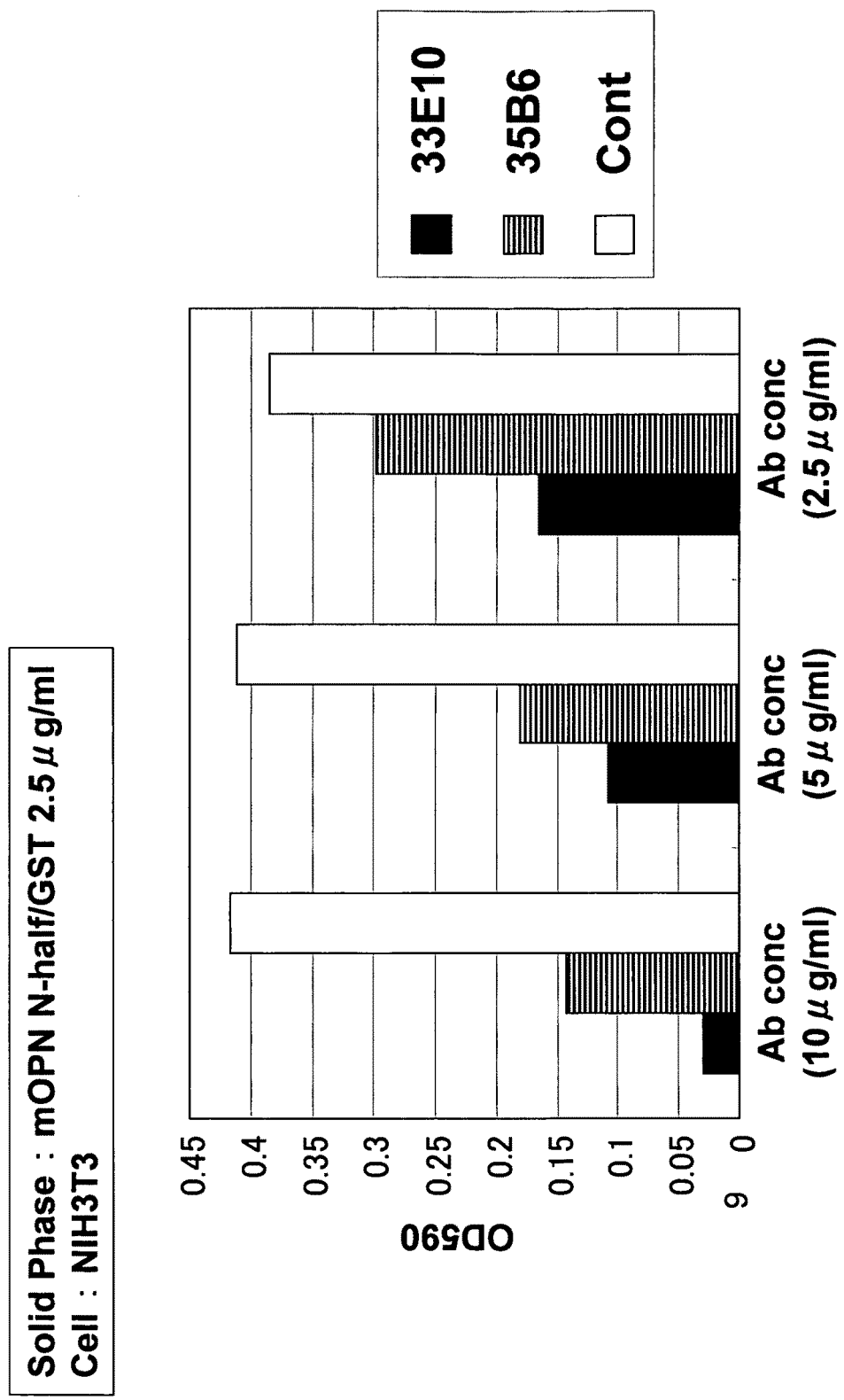
FIG. 9 shows the effect of anti-RGD antibodies to inhibit cell adhesion between mOPN N-half and cancer cell (NIH3T3 cell).

A mixture of NIH3T3 cells and monoclonal antibody 33E10 or 35B6 was added to 96-well plates on which mOPN N-half was immobilized, and examined the effect of the antibody on binding of NIH3T3 cells to mOPN N-half (FIG. 9). Further, a mixture of NIH3T3 cells and monoclonal antibody 33E10 was added to 96-well plates on which mOPN N-half, FN or VN was immobilized, and examined the effect of the antibody on binding of NIH3T3 cells to each of the proteins (FIG. 10).

Figure 10:
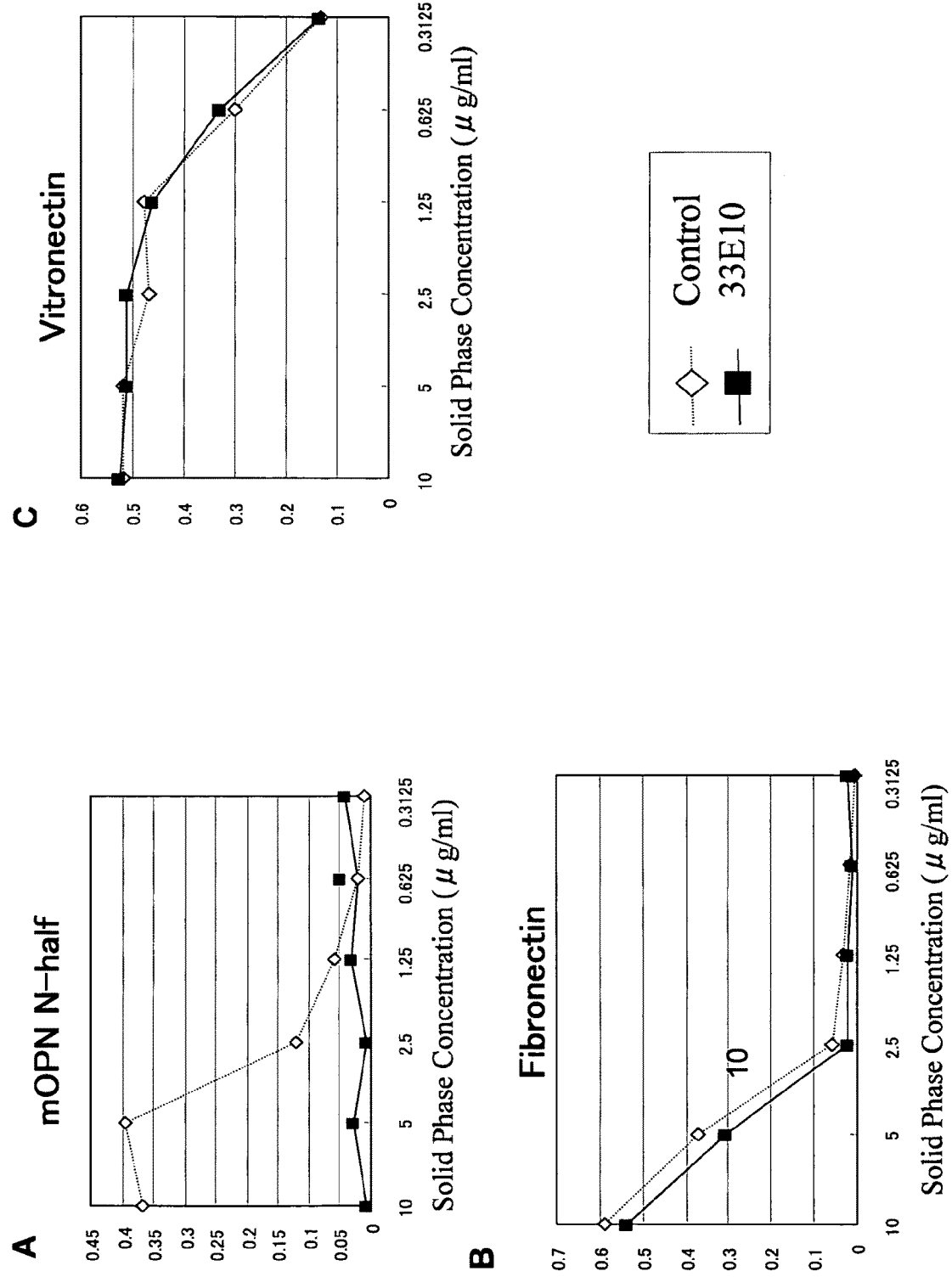
FIG. 10 shows the effect of anti-RGD antibody to inhibit cell adhesion between each of extracellular matrix proteins and tumor cell (NIH3T3 cell).

As shown in FIG. 9 and FIG. 10, NIH3T3 cells adhered to mOPN N-half and the cell adhesion was inhibited by anti-RGD antibodies. The monoclonal antibody 33E10 showed stronger RGD-dependent adhesion inhibitory activity compared to the monoclonal antibody 35B6. It was confirmed that NIH3T3 cells adhere to all the examined extracellular matrix proteins. The monoclonal antibody 33E10 inhibited cell adhesion with mOPN N-half, but did not inhibit cell adhesion with FN or VN. It suggests that the monoclonal antibody 33E10 specifically inhibits the adhesion between OPN and cells.

Example 6

Hepatitis Inhibition Test

[Hepatitis Model Animal]

Regarding hepatitis model, C57BL/6 mice were subjected to tail vein injection of concanavalin A (Con A) (200 μg/mouse), and 12 hours later, ALT and AST, which are markers of hepatitis, were examined.

[Therapeutic Effect on Hepatitis]

The mice were subjected to tail vein injection of monoclonal antibodies (400 μg/mouse), and 3 hours later, Con A was administered to the mice. 12 hours later, ALT and AST were measured. One group included 5 mice, and murine IgG was used as a control antibody.

Figure 11:
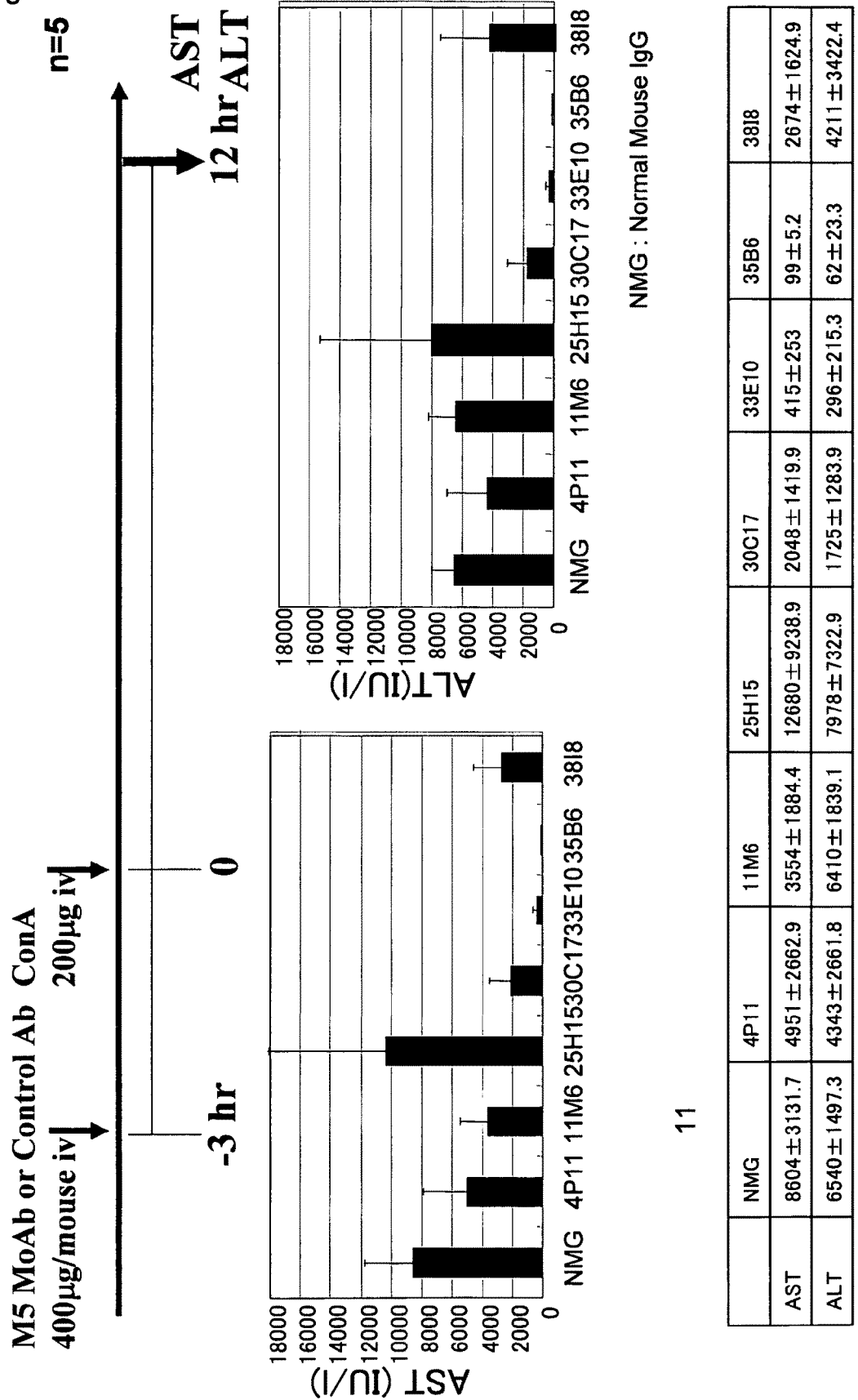
FIG. 11 shows the suppressive effect of anti-RGD antibodies to hepatitis.

Results are shown in FIG. 11. The monoclonal antibody 25H15 did not inhibit the onset of hepatitis at all. The monoclonal antibodies 4P11, 11M6, 29R5, 30C17 and 3818 showed slight inhibitory effect. In the case of the monoclonal antibodies 33E10 and 35B6, no elevated activity of ALT and AST was observed, and it suggests that these monoclonal antibodies inhibit the onset of hepatitis.

Example 7

Cancer Metastasis Inhibition Test

[Cancer Metastasis Model Animal]

Regarding experimental pulmonary metastasis model, C57BL/6 mice were subjected to tail vein injection of murine melanoma cell line B16-Luc cells (1×$10^5$ cells/mouse), and 14 days later, the number of pulmonary metastasis was counted.

Regarding spontaneous pulmonary metastasis model, C57BL/6 mice were subjected to subcutaneous injection of B16-BL6 cells (4×$10^5$ cells/mouse) in the right rear footpad. 19 days later, original tumor was surgically resected. 14 days after resection of original tumor (33 days after injection of B16-BL6 cells), the mice were sacrificed, and the number of tumor colonies in lung was counted.

[Cancer Metastasis Inhibitory Effect]

Regarding the experimental pulmonary metastasis model, a mixture of monoclonal antibodies (400 μg/mouse) and B16-Luc cells was administered to the mice, and 14 days later, the number of pulmonary metastasis was counted. Antibodies of the same subclass (mIgG1) were used as control antibodies.

As shown in FIG. 12, the average number of pulmonary metastasis was lower in the case of 33E10 and 35B6 compared to the control. The monoclonal antibody 35B6 significantly inhibited pulmonary metastasis.

Regarding the spontaneous pulmonary metastasis model, 200 μg/mouse of monoclonal antibodies were intraperitoneally administered 8 times at 3, 5, 7, 9, 11, 13, and 17 days after tumor transplantation, and the size of original tumor was measured until surgical resection was carried out 19 days after tumor transplantation. Further, 14 days after the surgical resection of original tumor, the number of tumor colonies in lung was counted. Antibodies of the same subclass (mIgG1) were used as control antibodies.

Figure 13:
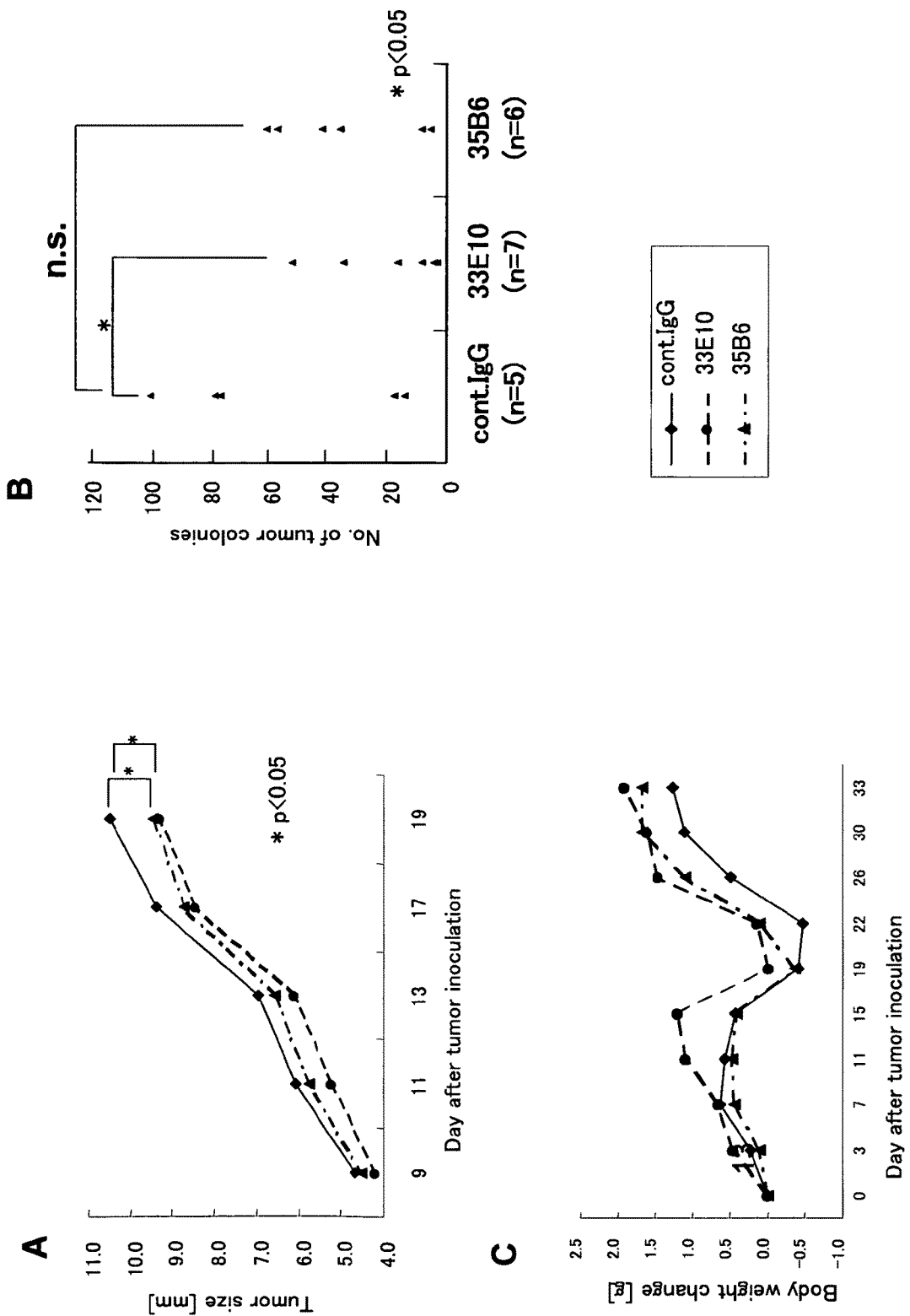
FIG. 13 shows the effect of anti-RGD antibodies to suppress pulmonary metastasis in spontaneous pulmonary metastasis model. In this Figure, A indicates the tumor size, B indicates the number of metastatic cells and C indicates the change of body weight.

The size variation of original tumor per day and the number of tumors (pulmonary metastasis) are shown in FIG. 13. The size of original tumor was significantly smaller in 33E10 or 35B6-administered mice compared to the control, and it was confirmed that both 33E10 and 35B6 have the effect to inhibit growth of tumor. Since two of five mice in control group had a number of metastasis tumors, statistically significant difference was not shown about 35B6. However, the average number of metastasis tumors was lower in the 33E10 or 35B6-administered mice compared to the control, and it suggests that both the monoclonal antibodies 33E10 and 35B6 inhibit pulmonary metastasis of cancer.

Example 8

Rheumatoid Arthritis Inhibition Test

[Rheumatoid Arthritis Model Animal]

Rheumatoid arthritis was caused to develop using a cocktail for joint (IBL) in which an antibody to anti-type II collagen was administered according to the supplier's instruction. That is, cocktail of anti-type II collagen antibody was administered to BALB/c mice, and 3 days later, LPS was administered to the mice to cause the disease to develop. For evaluation of arthritis, the levels of arthritis in respective paws were scored as follows: (0=no symptom; 1=swelling and reddening of only one small joint such as toe; 2=swelling and reddening of two or more small joints or a relatively large joint such as a wrist joint and a ankle joint; 3=swelling and reddening of one entire paw; 4=swelling of one entire paw reaches the maximum level; maximum score of one mouse (4 paws) is 16).

[Inhibitory Effect on Onset of Rheumatoid Arthritis]

Monoclonal antibodies (200 μg/day) were intraperitoneally administered to the mice 8 times in total during the period between the day before the administration of the cocktail for joint and 6 days after the administration of the cocktail for joint. The mice were observed everyday after the administration of the cocktail for joint to score the levels of arthritis.

Figure 14:
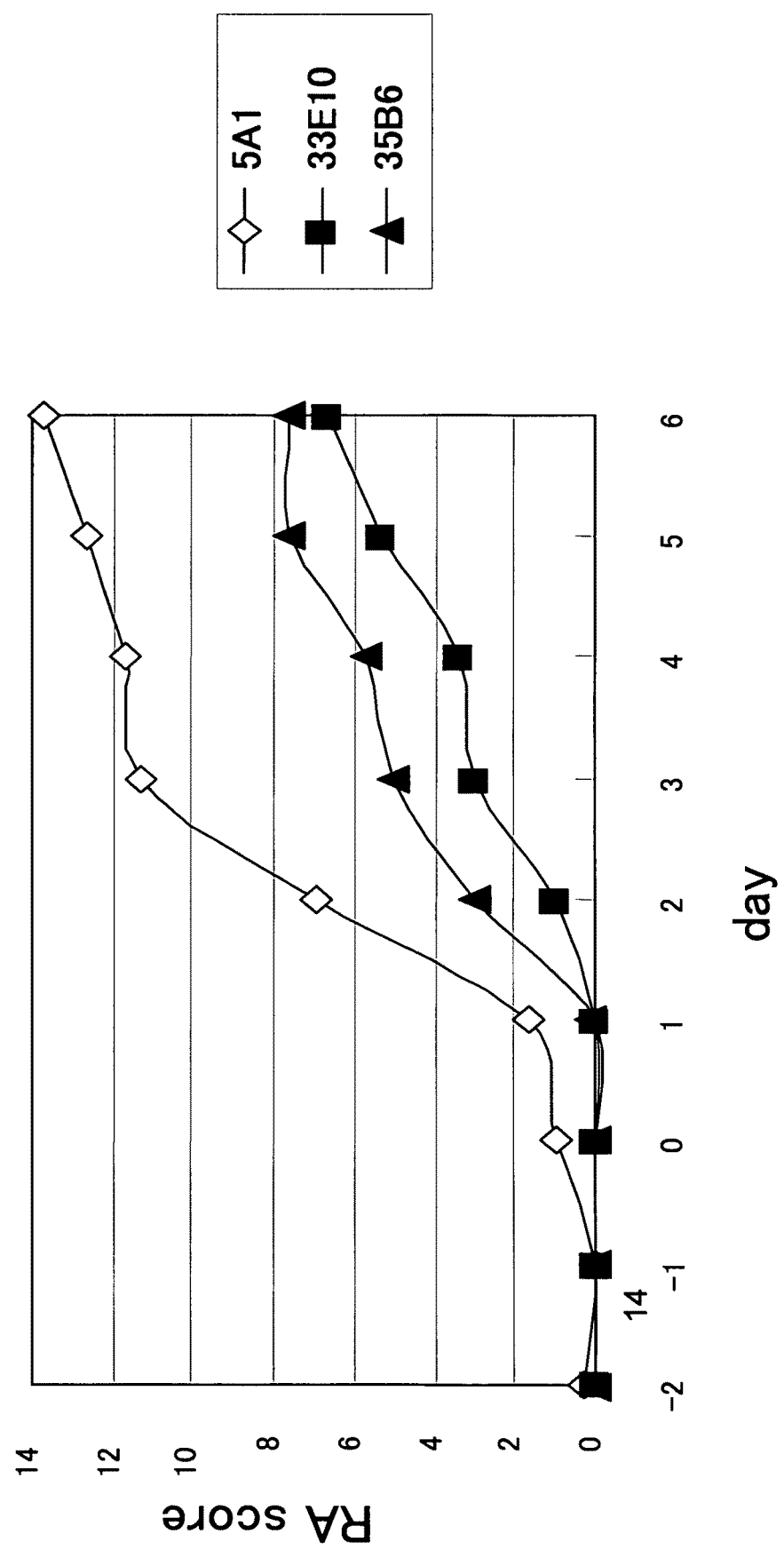
FIG. 14 shows the effect of anti-RGD antibodies to treat rheumatoid arthritis in rheumatoid model.

As shown in FIG. 14, both 33E10 and 35B6 had smaller score compared to the control, and it can be said that both 33E10 and 35B6 have the effect to inhibit rheumatoid arthritis.

INDUSTRIAL APPLICABILITY

The monoclonal antibody of the present invention inhibits the function of extracellular matrix proteins to exert therapeutic effects on cancer (e.g., proliferation and metastasis of tumor cells), inflammatory disease (e.g., osteoarthritis, hepatitis, bronchial asthma, fibrosis, diabetes, arteriosclerosis, multiple sclerosis, and inflammatory bowel disease (ulcerative colitis, Crohn's disease)), infection disease (e.g., hepatitis), autoimmune disease (e.g., rheumatoid arthritis, systemic lupus erythematosus, polymyositis, autoimmune thyroid disease, tubulointerstitial nephritis, and myasthenia gravis), bone disease (e.g., osteoporosis) or the like. Since the monoclonal antibody of the present invention can detect extracellular matrix proteins in body fluid, cells or tissue, it can be used as a diagnostic medicine.

---

The invention claimed is:

1. An isolated antibody comprising: the amino acid sequences of SEQ ID NOS: 1, 3, and 5 as CDRH1, CDRH2, and CDRH3, respectively, and the amino acid sequences of SEQ ID NOS: 7, 9, and 11 as CDRL1, CDRL2, and CDRL3, respectively; or the amino acid sequences of SEQ ID NOS: 2, 4, and 6 as CDRH1, CDRH2, and CDRH3, respectively, and the amino acid sequences of SEQ ID NOS: 8, 10, and 12 as CDRL1, CDRL2, and CDRL3, respectively.

2. An isolated antibody comprising the amino acid sequences of SEQ ID NOS: 1, 3, and 5 as CDRH1, CDRH2, and CDRH3 respectively, and the amino acid sequences of SEQ ID NOS: 7, 9, and 11 as CDRL1, CDRL2, and CDRL3, respectively.

3. An isolated antibody comprising the amino acid sequences of SEQ ID NOS: 2, 4, and 6 as CDRH1, CDRH2, and CDRH3, respectively, and the amino acid sequences of SEQ ID NOS: 8, 10, and 12 as CDRL1, CDRL2, and CDRL3, respectively.

4. The isolated antibody according to claim 2, which specifically recognizes an amino acid sequence comprising the RGD sequence of extracellular matrix proteins of a human and/or a mouse.

5. The isolated antibody according to claim 1, which is a monoclonal antibody.

6. The isolated antibody according to claim 1, which inhibits binding of human and/or a mouse osteopontin to an RGD receptor.

7. The isolated antibody according to claim 1, which is a chimeric antibody.

8. The isolated antibody according to claim 1, which is a humanized antibody.

9. An isolated monoclonal antibody produced by a hybridoma cell of Accession No. FERM BP-10440 or FERM BP-10441.

10. A therapeutic medicine for cancer, inflammatory diseases, hepatitis, autoimmune diseases or osteoporosis, comprising the antibody according to claim 1 as an active component.

11. A diagnostic medicine for cancer, inflammatory diseases, autoimmune diseases or osteoporosis, comprising the antibody according to claim 1 as an active component.

12. A method for producing the antibody according to claim 1, wherein CVDVPNGRGDSLAYGLR (SEQ ID NO: 13) is used as an antigen.

13. A method for producing a chimeric antibody in which the complementary determining regions of the antibody according to claim 1 and adjacent murine variable domain framework regions are incorporated into a human antibody by means of gene engineering.

14. A method for producing a humanized antibody in which the complementary determining regions of the antibody according to claim 1 are incorporated into a human antibody by means of gene engineering.

* * * * *